United States Patent
Peterson

(10) Patent No.: US 10,285,854 B2
(45) Date of Patent: May 14, 2019

(54) INTEGRATED OCLULAR FLUID MANAGEMENT SYSTEM

(71) Applicant: Medical Instrument Development Laboratories, Inc., San Leandro, CA (US)

(72) Inventor: Erik William Peterson, Walnut Creek, CA (US)

(73) Assignee: Medical Instrument Development Laboratories, Inc., San Leandro, CA (US)

( * ) Notice: Subject to any disclaimer, the term of this patent is extended or adjusted under 35 U.S.C. 154(b) by 0 days.

(21) Appl. No.: 15/599,665

(22) Filed: May 19, 2017

(65) Prior Publication Data
US 2017/0252211 A1 Sep. 7, 2017

Related U.S. Application Data

(62) Division of application No. 14/109,513, filed on Dec. 17, 2013.

(51) Int. Cl.
*A61F 9/007* (2006.01)
*A61M 1/00* (2006.01)

(52) U.S. Cl.
CPC ........ *A61F 9/00736* (2013.01); *A61M 1/006* (2014.02); *A61M 1/0031* (2013.01);
(Continued)

(58) Field of Classification Search
CPC .............. A61M 1/0031; A61M 1/0058; A61M 2205/3306; A61M 1/1037; A61M 1/1039;
(Continued)

(56) References Cited

U.S. PATENT DOCUMENTS 4,261,356 A 4/1981 Turner et al.
4,715,786 A 12/1987 Wolff et al.
(Continued)

FOREIGN PATENT DOCUMENTS

CN 1951346 4/2007
CN 101146498 3/2008
(Continued)

OTHER PUBLICATIONS

PCT/US2014/069018 International Search Report and Written Opinion of the International Searching Authority dated Mar. 16, 2015 (12 pages).
(Continued)

*Primary Examiner* — Bhisma Mehta
*Assistant Examiner* — William R Frehe
(74) *Attorney, Agent, or Firm* — Michael Best & Friedrich LLP

(57) ABSTRACT

An integrated ocular fluid management system that, in one instance, includes a first chamber connected to a first input line and a first output line. A second chamber is connected to a second input line and a second output line. A first pump communicates with the first output line. A second pump communicates with the second input line. A first pressure regulator communicates with the first chamber. A second pressure regulator communicates with the second chamber. A first diaphragm is in the first chamber; and a second diaphragm is in the second chamber. A first controller controls at least one of the first pump and the first pressure regulator to maintain the first diaphragm in a predetermined position. A second controller controls operation of at least one of the second pump and the second pressure to maintain the second diaphragm in a predetermined position.

7 Claims, 19 Drawing Sheets

(52) U.S. Cl.
CPC ... *A61M 1/0058* (2013.01); *A61M 2205/3344* (2013.01); *A61M 2210/0612* (2013.01)

(58) Field of Classification Search
CPC ... A61M 1/006; A61M 1/0062; A61M 1/0064
See application file for complete search history.

(56) References Cited

U.S. PATENT DOCUMENTS

| | | | |
|---|---|---|---|
| 4,722,350 A | 2/1988 | Armeniades | |
| 4,770,654 A | 9/1988 | Rogers et al. | |
| 5,157,603 A | 10/1992 | Scheller et al. | |
| 5,352,180 A | 10/1994 | Candelon et al. | |
| 5,354,268 A * | 10/1994 | Peterson | A61M 1/0031 604/319 |
| 5,380,280 A | 1/1995 | Peterson | |
| 5,520,652 A | 5/1996 | Peterson | |
| 7,984,318 B2 | 7/2011 | Fu et al. | |
| 8,246,580 B2 | 8/2012 | Hopkins et al. | |
| 8,439,874 B2 | 5/2013 | Hertweek | |
| 2005/0245903 A1 | 11/2005 | Kuklin et al. | |
| 2006/0224143 A1 | 10/2006 | Claus et al. | |
| 2008/0114300 A1 | 5/2008 | Muri et al. | |
| 2008/0114372 A1* | 5/2008 | Edwards | A61M 1/0005 606/107 |
| 2008/0275377 A1 | 11/2008 | Paolini et al. | |
| 2009/0096336 A1 | 4/2009 | Petrick et al. | |
| 2009/0118663 A1 | 5/2009 | Rockley et al. | |
| 2009/0163852 A1 | 6/2009 | Cull | |
| 2009/0182266 A1 | 7/2009 | Gordon et al. | |
| 2010/0191178 A1* | 7/2010 | Ross | A61F 9/00736 604/22 |
| 2010/0280434 A1 | 11/2010 | Raney et al. | |
| 2010/0280435 A1* | 11/2010 | Raney | A61F 9/00745 604/22 |
| 2011/0071454 A1 | 3/2011 | Dos Santos | |
| 2011/0092891 A1* | 4/2011 | Gerg | A61F 9/00745 604/28 |
| 2011/0145445 A1 | 6/2011 | Malamant et al. | |
| 2011/0223581 A1 | 9/2011 | Stobbe | |
| 2011/0273144 A1 | 11/2011 | Yu et al. | |
| 2012/0065580 A1 | 3/2012 | Gerg et al. | |
| 2012/0084592 A1 | 4/2012 | Lin et al. | |
| 2012/0089080 A1* | 4/2012 | Ross | A61M 1/0037 604/22 |
| 2012/0116173 A1 | 5/2012 | Viola | |
| 2012/0120380 A1 | 5/2012 | Lyons | |
| 2012/0166173 A1 | 6/2012 | Fischbach | |
| 2012/0277779 A1 | 11/2012 | Kadzlauskas et al. | |
| 2013/0046228 A1 | 2/2013 | Bourne | |
| 2013/0060210 A1* | 3/2013 | Ross | A61M 1/0035 604/318 |
| 2013/0123680 A1 | 5/2013 | Ha et al. | |
| 2013/0211435 A1 | 8/2013 | Boukhny et al. | |
| 2013/0270165 A1 | 10/2013 | Shevitz | |
| 2015/0306286 A1* | 10/2015 | Ross | A61F 9/00745 604/22 |
| 2016/0367735 A1* | 12/2016 | Eddo | A61M 1/0064 |

FOREIGN PATENT DOCUMENTS

| | | |
|---|---|---|
| CN | 101903053 | 12/2010 |
| CN | 102472614 | 5/2012 |
| CN | 102946833 | 2/2013 |
| CN | 103298538 | 9/2013 |
| EP | 0180317 | 5/1986 |
| EP | 2786773 | 10/2014 |
| GB | 2465479 | 5/2010 |
| WO | 1993018802 | 9/1993 |
| WO | 200023020 | 4/2000 |
| WO | 2010054207 | 5/2010 |
| WO | 2012/092018 | 7/2012 |

OTHER PUBLICATIONS

Office Action from the US Patent and Trademark Office for U.S. Appl. No. 14/109,513 dated Dec. 14, 2017 (18 pages).
Chinese Patent Office Action for Application No. 201480074689.0 dated Feb. 1, 2018 (21 pages, English translation included).
EP14870793.8 Extended European Search Report dated Aug. 30, 2017 (7 pages).
United States Patent Office Action for U.S. Appl. No. 14/109,513 dated Apr. 20, 2018 (11 pages).

* cited by examiner

INTEGRATED OCLULAR FLUID MANAGEMENT SYSTEM

RELATED APPLICATIONS

This application claims priority to and is a divisional of U.S. application Ser. No. 14/109,513, filed on Dec. 17, 2013, the entirety of which is hereby incorporated by reference.

FIELD

Embodiments of the invention relate to ocular fluid management systems. More particularly, embodiments of the invention relate to a fluid management system that senses the position of a diaphragm and operates in one or more operating modes.

BACKGROUND

Fluid management systems, such as aspiration systems and infusion systems, are commonly used during ophthalmic procedures. An aspiration system removes fluids from a patient's eye. In contrast, an infusion system supplies fluids to the patient's eye. An integrated fluid management system provides both aspiration and infusion functions under common control. The operator can control the amount of pressure or suction applied by each system using a foot pedal, control panel settings, or a combination of both. However, particular situations occurring during a procedure require quick and efficient operation of the system, which may be difficult to perform manually. For example, if an aspiration system encounters a substance or obstruction that it cannot remove (e.g., a non-fluid substance or a dense substance), the obstruction often causes the aspiration system to lose proper suction. In this situation, the obstruction must be quickly and efficiently handled to resume proper operation of the aspiration system.

SUMMARY

Coordinated operation of the aspiration and infusion systems (as with an integrated fluid management system) is very important for patient safety. In modern ophthalmic surgical procedures, the eye is more or less a closed vessel (with some leakage). An excess of infusion over aspiration can cause an elevation of pressure in the eye, which can reduce perfusion of blood to the retina, among other consequences. An excess of aspiration over infusion can cause a reduction of pressure in the eye, and even collapse of certain structures. In the anterior chamber of the eye (between the cornea and the lens), collapse of the cornea and damage to the corneal endothelium with resulting opacity of the cornea are potential hazardous situations associated with improper pressure. In the posterior chamber of the eye (behind the lens), partial collapse of the globe, detachment of the choroid, and resulting hemorrhage are other serious situations associated with improper pressure.

At the very least, aspiration must not be allowed to occur if infusion is inactive. Therefore, means to ensure that infusion flow is always at least equal to aspiration flow (or slightly higher, to compensate for leakage) is highly desirable. In typical ophthalmic surgical systems, however, one or both of these flows is not measurable, so more indirect means are used to avoid hazardous situations. One object of certain embodiments of the invention is to provide an integrated fluid management system in which both the aspiration flow and the infusion flow can be determined.

Cataract surgery presents a particularly challenging situation. The procedure is performed inside of the anterior chamber of the eye. As noted above, excess of aspiration over infusion can lead to opacification of the cornea. The volume of the anterior chamber is very small, approximately 0.3 milliliters, so small imbalances in the fluid management system can quickly lead to a hazardous situation.

Cataract surgery is further complicated by the trend to use less ultrasonic power (to reduce potential injury) and to compensate by using higher vacuum levels in the aspiration system. In a typical procedure, aspiration is used to attract fragments of the lens to the tip of the surgical instrument. Once the lens fragment is firmly seated against the opening in the tip of the instrument (occlusion) the aspiration flow is obstructed and the vacuum level at the instrument tip increases. The combination of the increased vacuum and ultrasonic vibration of the instrument tip breaks up the lens material into fragments small enough to pass through the opening in the tip of the instrument (break of occlusion). With the aspiration path no longer obstructed, aspiration flow accelerates under the influence of the vacuum present. With the trend to use higher vacuum levels, this acceleration of flow (surge) is even more rapid and hazardous. Thus, an additional object of certain embodiments of the invention is to provide an aspiration system in which the break of occlusion surge is inherently limited to a volume less than the volume of the anterior chamber, e.g., less than 0.3 milliliters.

Aspiration systems used in ophthalmic surgery have been classified by the parameter (vacuum or flow) that is most directly controlled by the surgeon. Typically, the surgeon uses a proportional foot pedal control to vary the chosen parameter between zero and some maximum level that has been preset on the surgical system control panel.

Surgeons generally use a vacuum-controlled mode or a flow-controlled mode. The selected mode can be based on the type of surgical procedure being performed and/or surgeon preference. Earlier ophthalmic surgical systems were only capable of operating in one mode of aspiration control. Flow-controlled systems were typically used for cataract surgery and vacuum-controlled systems were typically used for vitreoretinal surgery. A recent trend is surgical systems in which the user can select either a vacuum-controlled mode of operation or a flow-controlled mode of operation. Some such systems have two completely separate aspiration systems (i.e., one of each type). Other systems do have means to operate a single aspiration system either as flow-controlled or as vacuum-controlled. However, such systems typically involve compromises, with one or both modes having lesser performance than an aspiration system dedicated to one mode of operation. One object of certain embodiments of the invention is to provide an aspiration system capable of operation in a flow-controlled mode, a vacuum-controlled mode, and new modes that have characteristics of both flow-controlled and vacuum-controlled modes.

Accordingly, embodiments of the invention provide systems and methods for controlling ocular fluid management systems. One fluid management system includes a chamber with a first portion and a second portion. A flexible diaphragm is contained in the chamber and changes position based on a pressure difference between the two portions. The system can operate in one or more modes and includes a system controller. Within each mode, a system controller automatically operates the system. In particular, in one or more of the modes, the system controller is configured to maintain the diaphragm in a predetermined position. In some embodiments, the system controller operates a peristaltic pump and a vacuum pump to maintain the diaphragm in the predetermined position. In some embodiments, the system controller is also configured to detect an occlusion break based on a position of the diaphragm.

In particular, one embodiment of the invention provides an ocular fluid management system. The system includes a chamber, a diaphragm, a sensor, and a controller. The chamber includes a first portion and a second portion. The first portion is connected to an input line for receiving fluids into the first portion and an output line for discharging fluids from the first portion. The diaphragm is contained in the chamber and is configured to change position based on a pressure difference between the first portion and the second portion. The sensor detects a position of the diaphragm and transmits a signal based on the detected position. The controller is configured to receive the signal and control operation of at least one of a peristaltic pump and a vacuum pump based on the signal to maintain the diaphragm in a predetermined position.

Another embodiment of the invention provides a method of operating an ocular fluid management system. The method includes receiving, by a controller, a signal from a sensor detecting a position of a flexible diaphragm contained in a chamber. The flexible diaphragm changes position based on a pressure difference between a first portion of the chamber and a second portion of the chamber. The first portion of the chamber is connected to an input line for receiving fluids into the first portion and an output line for discharging fluids from the first portion. The method also includes controlling, by the controller, at least one of a peristaltic pump and a vacuum pump based on the signal to maintain the diaphragm in a predetermined position.

Other aspects of the invention will become apparent by consideration of the detailed description and accompanying drawings.

DETAILED DESCRIPTION

Figure 1:
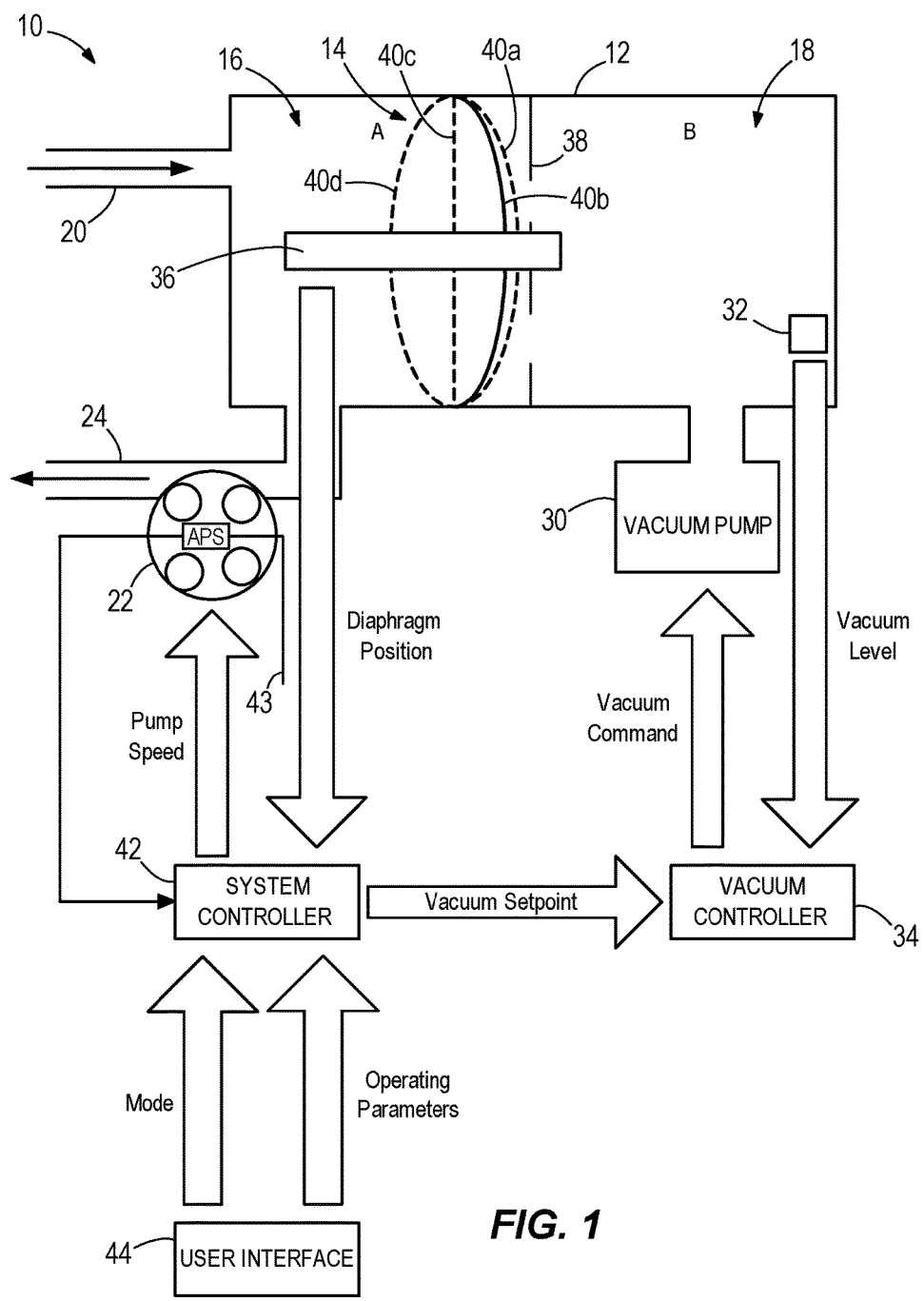
FIG. 1 schematically illustrates a fluid management system and, more particularly, an aspiration system.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. The terms "mounted," "connected," and "coupled" are used broadly and encompass both direct and indirect mounting, connecting and coupling. Further, "connected" and "coupled" are not restricted to physical or mechanical connections or couplings, and can include electrical connections or couplings, whether direct or indirect. Also, electronic communications and notifications may be performed using any known means including direct connections, wireless connections, etc.

It should be noted that a plurality of hardware and software based devices, as well as a plurality of different structural components may be utilized to implement the invention. Furthermore, and as described in subsequent paragraphs, the specific configurations illustrated in the drawings are intended to exemplify embodiments of the invention and that other alternative configurations are possible.

FIG. 1 illustrates a fluid management system 10. In many of the paragraphs that follow, the fluid management system 10 is operated or configured as an aspiration system. However, as is also explained below, the system 10 may also be operated or configured as an infusion system.

The system 10 includes a chamber 12. A flexible diaphragm 14 divides the chamber 12 into a first portion 16 (illustrated as portion "A" in FIG. 1) and a second portion 18 (illustrated as portion "B" in FIG. 1). The first portion 16 is connected with an input or aspiration line 20 that collects fluid from a patient's eye during a surgical operation. The first portion 16 of the chamber 12 is also connected with a pump 22. In one embodiment, the pump 22 is a peristaltic pump. In other embodiments, other pumping means may be used. The peristaltic pump 22 is connected to an output or discharge line 24. Fluid entering the chamber 12 from the aspiration line 20 exits the chamber 12 through the discharge line 24, which empties into a collection bag (not illustrated).

A vacuum pump 30 (or, more generically, a pressure regulator or pressure regulating means) is also connected to the chamber 12. In particular, the vacuum pump 30 is connected to the second portion 18 of the chamber. A vacuum sensor 32 (or, more generally, a pressure sensor) communicates with the chamber 12 (e.g., with the second portion 18). The vacuum sensor 32 provides a signal representing the vacuum level in the chamber 12 (e.g., an amount of pressure in the second portion 18 of the chamber 12). The signal from the vacuum sensor 32 is provided to a vacuum controller 34. The vacuum controller 34 uses the signal from the sensor 32 to operate the vacuum pump 30 (e.g., to establish a particular vacuum level in the chamber 12). Accordingly, the vacuum sensor 32 provides feedback to the vacuum controller 34, and the vacuum controller 34 uses the feedback to adjust the operation of the vacuum pump 30 (e.g., by sending a vacuum command to the pump 30). The vacuum pump 30 may be constructed using a peristaltic pump (distinct from the pump 22), a sensor for sensing pressure level (which may be the sensor 32), and a controller (such as the vacuum controller 34).

As illustrated in FIG. 1, a sensor 36 detects a position of the diaphragm 14 and outputs a signal representing the detected position of the diaphragm 14. The diaphragm 14 changes position based on a pressure difference between the first portion 16 and the second portion 18. As discussed in greater detail, multiple possible positions of the diaphragm 14 are illustrated in FIG. 1. A barrier 38 is also included in the chamber 12 that limits motion of the diaphragm 14 in at least one direction.

The position of the diaphragm 14 is considered "limited" when the diaphragm 14 is in contact with the barrier 38 (see the dashed line 40a illustrated in FIG. 1). A position of the diaphragm is considered "normal" when the diaphragm is stabilized close to its limited position but the diaphragm 14 is not in contact with the barrier 38 (see the solid line 40b illustrated in FIG. 1). The volume displaced by the movement of the diaphragm 14 from the normal position 40b to the limited position 40a (i.e., the volume gained in the first portion 16 due to the movement of the diaphragm 14) is called the "limited volume." The other dashed lines illustrated in FIG. 1 represent two additional positions of the diaphragm 14. For example, the straight dashed line 40c represents a "neutral" position of the diaphragm 14, and the curved dashed line 40d represents a "maximum portion B volume" position.

The vacuum in the second portion 18 of the chamber 12 acts on the flexible diaphragm 14 to draw the diaphragm 14 toward the second portion 18. The movement of the diaphragm 14 causes an increasing vacuum level in the fluid in the first portion 16 of the chamber 12. An equilibrium is reached when the vacuum in the first portion 16 of the chamber 12 acts on the diaphragm 14 with a force equal to the force exerted on the diaphragm by the vacuum in the second portion 18 of the chamber 12 minus any elastic force required to displace the flexible diaphragm 14 from its neutral position 40c. If the diaphragm 14 is highly flexible, this elastic force is small and the vacuum level in the first portion 16 of the chamber 12 will approximate the vacuum level in the second portion 18.

The vacuum in the first portion 16 of the chamber 12 causes suction of fluid through the aspiration line 20. The peristaltic pump 22 acts to remove fluid from the first portion 16 through discharge line 24. If and only if the outflow through the discharge line 24 equals the inflow through the aspiration line 20, the volume of fluid in the first portion 16 of the chamber will remain constant and the position of diaphragm 14 will not change. Any imbalance between outflow and inflow will cause the position of the diaphragm 14 to change over time.

As illustrated in FIG. 1, the signal output from the diaphragm position sensor 36 is received at a system controller 42. As described in more detail below, the system controller 42 uses the signal from the sensor 36 and other feedback to operate the fluid management system 10. The system controller 42 can also control the peristaltic pump 22 by providing operating parameters to the pump 22 (e.g., a pump speed and/or outflow rate). Similarly, the system controller 42 can provide operating parameters to the vacuum controller 34. As described in more detail below, in some embodiments, the system controller 42 controls operation of the peristaltic pump 22 and/or the vacuum pump 30 to return and/or maintain the diaphragm at a predetermined position, such as the normal position 40b.

For peristaltic pump 22, there is a relationship between the rotational speed of the pump motor (e.g., RPM) and the flow through the pump (e.g., milliliters/minute). This relationship can be estimated from geometric considerations, or can be determined empirically. The system controller 42 typically has direct control over the rotational speed of peristaltic pump 22, but receives setpoint information or reports data in terms of flow. Besides rotational speed, angular position affects flow. In some embodiments, an average of flow over an entire rotation of the peristaltic pump 22 is used for calculations by the system controller 42. In other embodiments, system controller 42 receives a signal from angular position sensor 43. In some embodiments, the motor driving peristaltic pump 22 is a stepping type and position sensor 43 provides an indexing pulse each time that the motor returns to a fixed position, thereby allowing angular position to be determined as the number of steps since the last indexing pulse. Based on the angular position information, a more exact relationship between rotational speed and flow can be calculated. In particular, system controller 42 may adjust rotational speed in accordance with position so as to maintain a more nearly constant flow rate through peristaltic pump 22.

The system controller 42 receives input from an operator through a user interface 44. The input can include an operating mode selection. The input can also receive operating parameters for a selected operating mode. Each operating mode of the fluid management system 10 can be associated with one or more operating parameters. During operation, the system controller 42 controls and monitors operation of the fluid management system 10 based on the operating parameters. Additional details regarding the operating parameters are provided below. The operating parameters are typically set by an operator before an ophthalmic procedure. The system controller 42, however, can also receive real-time operating parameters from a user during an ophthalmic procedure, such as through a foot pedal.

It should be understood that the system controller 42 can include additional components than those described herein. In addition, in some embodiments, the functionality of the system controller 42 can be distributed among multiple systems or devices. Also, in some embodiments, the functionality of the system controller 42 can be combined with other systems or devices. For example, in some embodiments, the system controller 42 also performs the functionality of the vacuum controller 34. In one such embodiment, the functions of the system controller 42 and the vacuum (or pressure) controller 34 are combined in a single controller that directly or indirectly receives signals from the position sensor 36 and the vacuum sensor 32.

In a first state of operation (e.g., a vacuum-controlled state), the system controller 42 responds to inputs through the operator interface 44 to set the vacuum setpoint. Vacuum controller 34 operates vacuum pump 30 so as to maintain the output of vacuum sensor 32 at the vacuum setpoint level selected by the operator. Simultaneously, the system controller 42 adjusts the pump speed of peristaltic pump 22 to maintain the diaphragm 14 at a predetermined position, as determined by the signal from the diaphragm position sensor 36. The pump speed can be used to calculate the outflow rate through the discharge line 24, which must be equal to the inflow rate through the aspiration line 20. This assumed inflow rate may be displayed or otherwise used to affect the operation of the system.

In a second state of operation (e.g., a flow-controlled state), the system controller 42 responds to inputs through the operator interface 44 to set the pump speed corresponding to a flow rate selected by the operator. The peristaltic pump 22 operates at this pump speed, thereby maintaining the outflow rate through the discharge line 24 at the selected flow rate. Simultaneously, the system controller 42 adjusts the vacuum setpoint to vacuum controller 34 to maintain the diaphragm 14 at a predetermined position, as indicated by the signal from the diaphragm position sensor 36. The inflow rate through the aspiration line 20 should then be equal to the operator-selected outflow rate through the discharge line 24. The vacuum setpoint and/or the resulting actual vacuum signal from the vacuum sensor 32 may be displayed or otherwise used to affect the operation of the system.

In either state of operation, occlusion of the aspiration line 20 can result in a high applied vacuum and little or no flow. If the occlusion is abruptly removed, flow through aspiration line 20 will rapidly accelerate under the influence of the high vacuum. While both modes of operation have mechanisms to counteract this surge in inflow, there is a finite response time. Therefore, it is likely that there will be a temporary loss of control. As noted, uncontrolled aspiration flow is particularly hazardous in cataract surgery, where a surge of only 0.3 milliliters volume can result in collapse of the anterior chamber of the eye.

As illustrated in FIG. 1, the barrier 38 limits the movement of the diaphragm 14 to the "limited" position shown as 40a. The control mechanisms in either the first or second modes of operation (e.g., the vacuum controller 34 and the peristaltic pump 22) act to maintain the diaphragm 14 in the "normal" position shown as 40b. Thus, the maximum volume change during a loss of control situation (i.e., the volume change in the first portion 16 of the chamber due to the movement of the diaphragm 14) is the volume contained between position 40b and position 40a of the diaphragm. Based on the anatomy of the human eye, this "limited volume" should be designed to be less than 0.3 milliliters. However, the "limited volume" can be adjusted when embodiments of the invention are applied to different anatomies.

In some embodiments, the system controller 42 may employ a third state of operation (e.g., a break of occlusion state) to return through the aspiration line 20 some of the volume which may have been lost from the eye during the uncontrolled surge. The third state of operation is entered (from either the first or second state of operation) whenever there is a loss of control, as indicated by a change in the signal from diaphragm position sensor 36 corresponding to a significant movement of the diaphragm from position 40b towards position 40a. In this third mode of operation, the system controller 42 sets the vacuum setpoint at a predetermined low level and sets the pump speed of the peristaltic pump 22 to a predetermined high speed in the reverse direction (causing flow through the discharge line 24 to be directed into the first portion 16 of the chamber.) The third mode of operation is exited (to the previous mode of operation) after a period of time such that this reverse flow accumulates to a volume approximately equal to the "limited volume" discussed above. In either the first or second modes of operation, the system controller 42 will then act to restore the diaphragm 14 to the "normal" position 40b.

Figure 2:
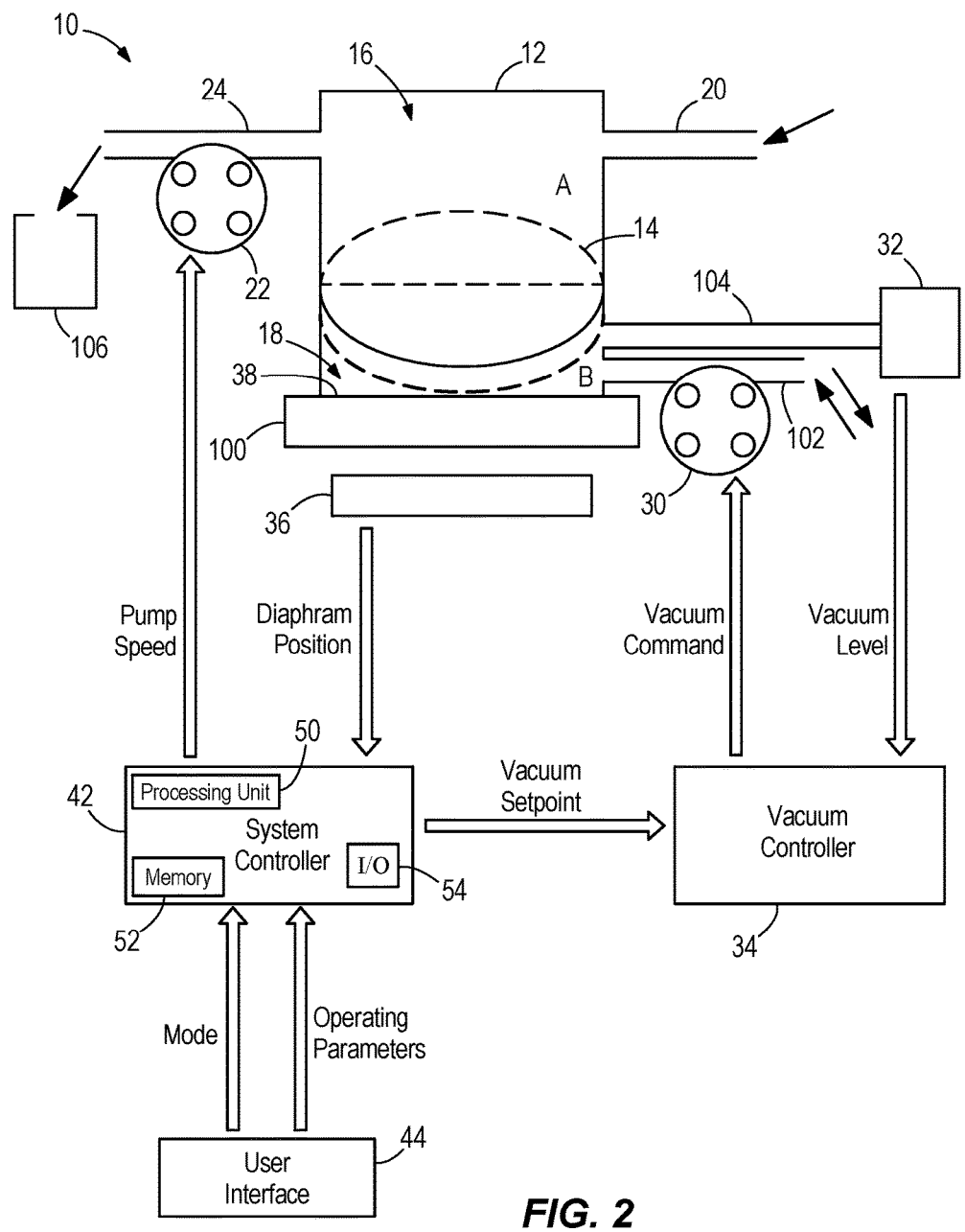
FIG. 2 schematically illustrates another embodiment of an aspiration system.

FIG. 2 illustrates another embodiment of fluid management system 10. In this embodiment, the diaphragm position sensor 36 is a non-contacting, optical-type sensor positioned to view the diaphragm 14 through a transparent window 100. The transparent window 100 also serves as the barrier 38 and as part of the enclosure of chamber 12. In addition to peristaltic pump 22 (connected through discharge line 24 to collection bag 106) the vacuum pump 30 is also a peristaltic type pump. The vacuum pump 30 is connected to the second portion 18 of the chamber 12 and also to the atmosphere through vent line 102. Vacuum controller 34 operates vacuum pump 30 bi-directionally. Pumping air from the chamber 12 to the vent line 102 increases the vacuum level in the second portion 18 of the chamber, and pumping air from the vent line 102 to the chamber 12 decreases the vacuum level. Vacuum sensor 32 communicates with the second portion 18 of the chamber 12 through vacuum port 104, providing a feedback signal to the vacuum controller 34. The first portion 16 of chamber 12 is also connected through aspiration line 20 to various surgical instruments used in the patient's eye during a surgical operation.

The system controller 42 may be configured in a number of different ways and may include a processing unit 50 (e.g., a microprocessor, an application specific integrated circuit ("ASIC"), etc.), one or more memory modules 52, and an input/output interface 54. The memory modules 52 include non-transitory computer-readable medium, such as random-access memory ("RAM") and/or read-only memory ("ROM"). The processing unit 50 can retrieve instructions from the memory modules 52 and execute the instructions to perform particular functionality. The processing unit 50 can also retrieve and store data to the memory modules 52 as part of executing the instructions.

The processing unit 50 can obtain data from devices and systems external to the system controller 42 through the input/output interface 54. For example, as noted above, the system controller 42 receives signals from the diaphragm position sensor 36 and the user interface 44. The system controller 42 also provides output to the peristaltic pump 22 and the vacuum controller 34. Therefore, the input/output interface 54 connects the system controller 42 to the diaphragm position sensor 36, the user interface 44, the peristaltic pump 22, and the vacuum controller 34. It should be understood that the system controller 42 can be connected to these and other devices external to the system controller 42 using a wired connection or a wireless connection.

It should also be understood that the system controller 42 can include additional components than those described herein. Furthermore, in some embodiments, the functionality of the system controller 42 can be distributed among multiple systems or devices. Also, in some embodiments, the functionality of the system controller 42 can be combined with other systems or devices. For example, in some embodiments, the system controller 42 also performs the functionality of the vacuum controller 34.

The instructions executed by the processing unit 50 included in the system controller 42 control operation of the fluid management system 10. For example, in one embodiment, the fluid management system 10 can operate in one of a plurality of modes. The instructions executed by the processing unit 50 operate the fluid management system 10 in one of the modes based on the manual selection of an operating mode by a user (e.g., through the user interface 44). The instructions executed by the processing unit 50 can also receive operating parameters for a selected operating mode from an operator (e.g., a surgeon) through the user interface 44. The instructions executed by the processing unit 50 use the operating parameters and feedback to automatically operate the fluid management system 10 within the selected operating mode. Furthermore, in some embodiments, the instructions executed by the processing unit 50 automatically operate the fluid management system 10 in a particular mode based on feedback received by the system controller 42.

In some embodiments, the fluid management system 10 operates in one of three operating modes: (1) a vacuum control mode; (2) a flow control mode; and (3) an occlusion response mode. An operator can manually select one of the modes before an ophthalmic procedure. FIGS. 3-10 are a flowchart illustrating operation of the system 10 in each of the three modes. To allow the operator to select a particular mode, the user interface 44 displays a list of available operating modes (at block 100) and the operator can select one of the operating modes before (or during) an ophthalmic procedure (at block 102).

Pressure/Vacuum Control Mode

To operate the fluid management system 10 in the vacuum control mode, an operator selects the vacuum control mode from the list of operating modes presented on the user interface 44 (at block 104). The user interface 44 then prompts the operator to define operating parameters for the vacuum control mode (at block 106). For the vacuum control mode, the operator specifies or selects a maximum vacuum level ($V_{max}$). The maximum vacuum level represents the maximum vacuum level achievable when the foot pedal is in a lowest (i.e., fully engaged) position. In some embodiments, the operator also defines a minimum vacuum level ($V_{min}$). In other embodiments, the system controller 42 is preprogrammed or configured with a minimum vacuum level of zero. The minimum vacuum level represents the minimum vacuum level achievable when the foot pedal in a highest (i.e., minimally engaged) position. The system controller 42 derives a requested vacuum level ($V_{request}$) from the limits ($V_{min\ and}\ V_{max}$) and the position of the foot pedal between the minimally engaged and fully engaged positions. In some embodiments, the vacuum levels are specified in terms of millimeters of mercury ("mmHg").

In some embodiments, the operator also defines a maximum outflow rate for the peristaltic pump 22 ($F_{max}$) (e.g., in cubic centimeters per minute ("cc/min")) as an operating parameter. In other embodiments, the system controller 42 is preprogrammed or configured with the maximum achievable rate of the peristaltic pump 22.

In some embodiments, the user interface 44 displays a list of available values for each operating parameter or a list of available sets of values for the set of operating parameters. Furthermore, in some embodiments, the list of available values is customized based on the operator (e.g., linked to an operator identifier provided by the operator to the user interface 44, such as when the operator logs into the system 10).

In some embodiments, the vacuum control mode has two states: State 1 and State 2. State 1 is the initial state. In State 1, the operator can manually increase (or decrease) the vacuum level generated by the vacuum pump 30 by increasing (or decreasing) pressure on the foot pedal. In particular, in State 1, the operator operates the foot pedal to indicate a requested vacuum level ($V_{request}$). The manually-requested vacuum level is based on the maximum vacuum level and the current position of the foot pedal.

The system controller 42 receives the manually-requested vacuum level (at block 107) and provides the requested vacuum level to the vacuum controller 34. The vacuum controller 34 operates the vacuum pump 30 using a closed feedback loop to maintain the vacuum in the second portion 18 of the chamber 12 at the requested vacuum level (at block 108). An actual vacuum level ($V_{actual}$) is output by the vacuum sensor 32, which is provided to the vacuum controller 34 as feedback. In some embodiments, the actual vacuum level is also displayed on the user interface 44 or another display associated with the fluid management system 10. During normal operation, the actual vacuum level will be close to the requested vacuum level, but, in some situations, there may be a time lag between when the vacuum level is requested and when the requested vacuum level is achieved.

During State 1, the system controller 42 also operates the peristaltic pump 22 using a closed feedback loop to maintain the diaphragm 14 in the normal position (at block 110). A current diaphragm position is output by the sensor 36, which is provided to the system controller 42 as feedback.

Figure 4:
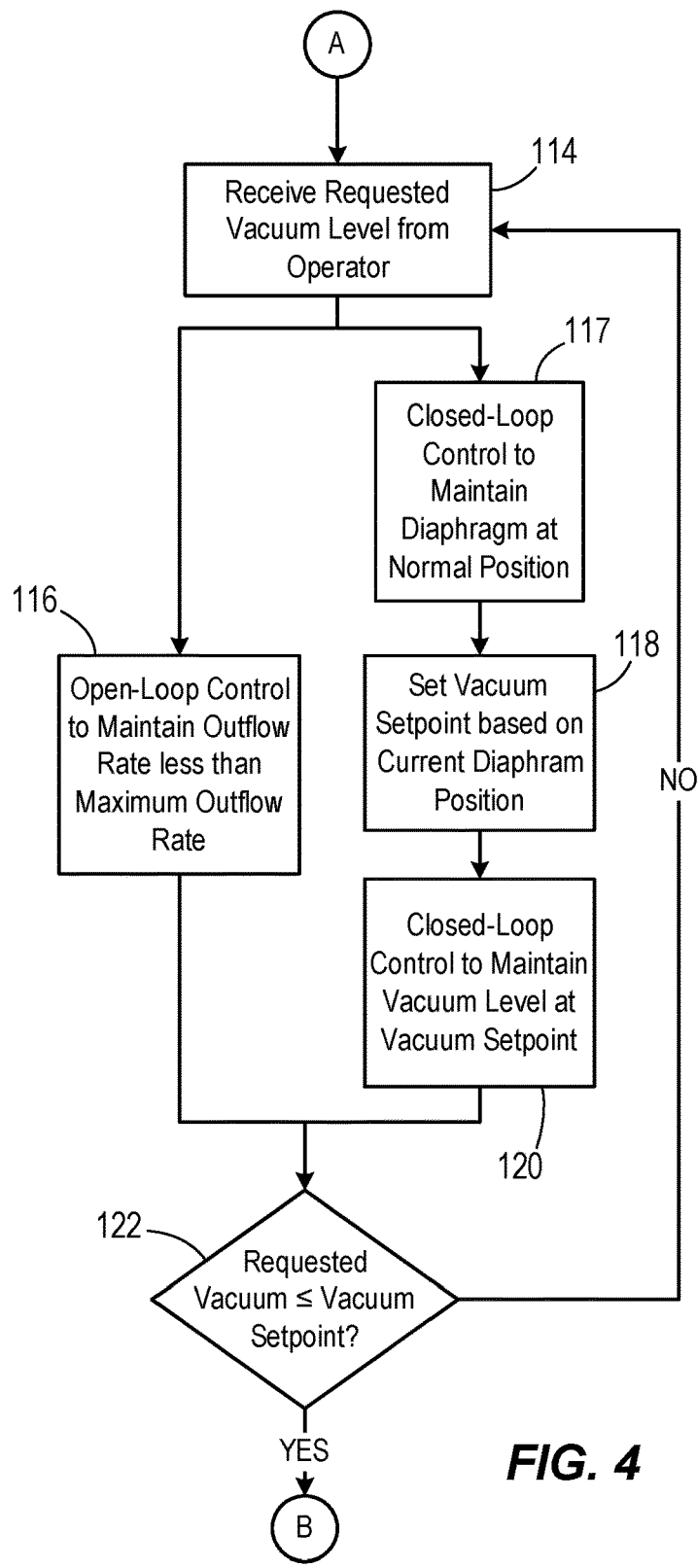
Figure 5:
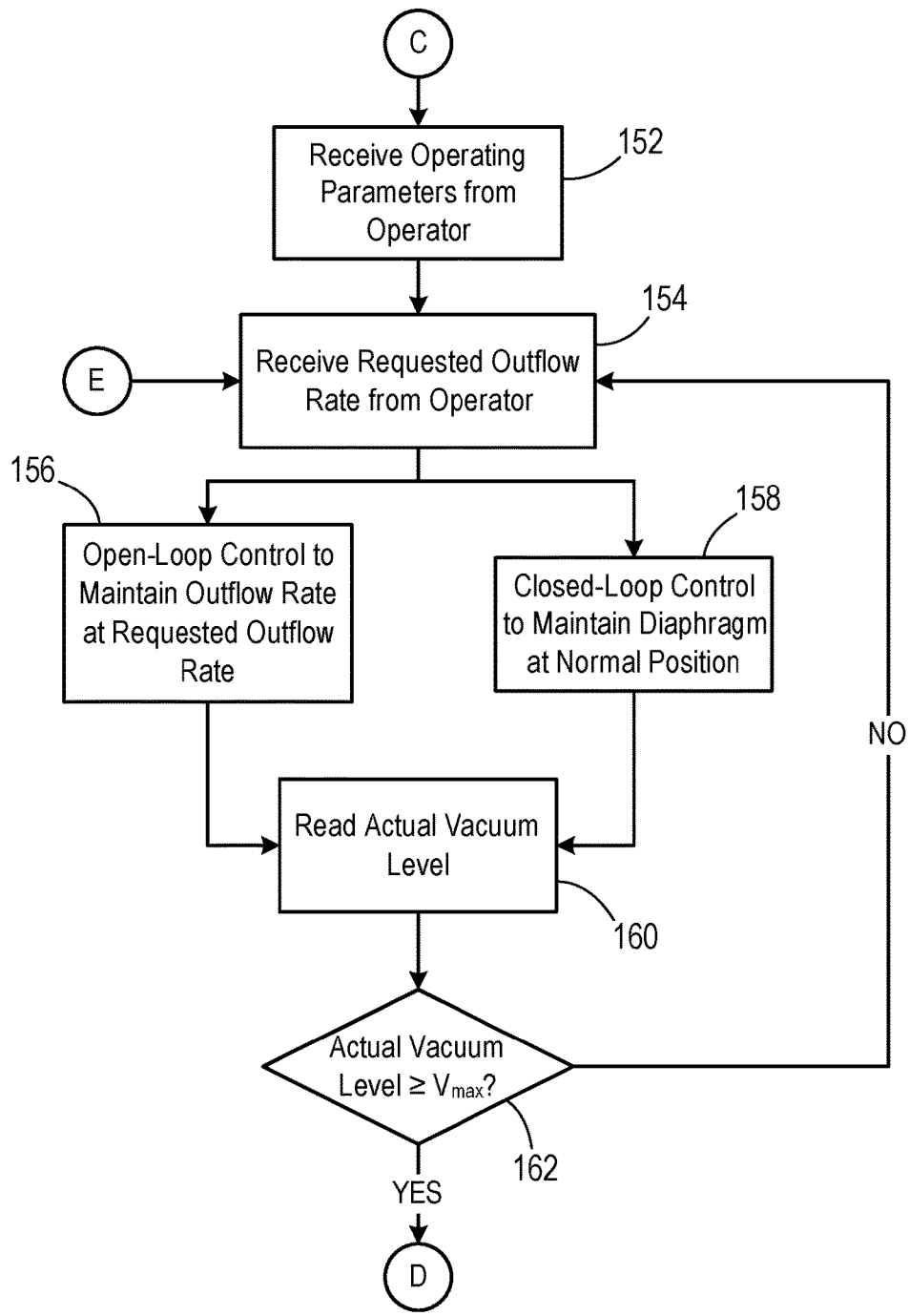

If the actual outflow rate ($F_{actual}$) of the peristaltic pump 22 rises to or exceeds the maximum outflow rate of the pump 22 ($F_{max}$) during State 1 (at block 112), the system controller 42 exits State 1 of the vacuum control mode and enters State 2 of the vacuum control mode (see FIG. 4). In some embodiments, there are two cases when the outflow rate of the peristaltic pump 22 rises to the maximum outflow rate. One case includes a vacuum-cleaning procedure when the operator wants to aspirate small drops of liquid from the operating field at the maximum outflow rate. In this case, State 2 of the vacuum control mode is prolonged and the operator disengages the foot pedal when the vacuum-cleaning procedure is finished. The other case occurs after an unusual event (e.g., a human error), such as when the maximum vacuum level is set too high for the aspiration system and the foot pedal is fully engaged. In this case, the duration of State 2 of the vacuum control mode should be as short as possible and the operator should quickly disengage the foot pedal.

In State 2 of the vacuum control mode, the operator operates the foot pedal to set a manually-requested vacuum level (at block 114, FIG. 4). However, as described in more detail below, the foot pedal does not control the vacuum level of the fluid management system 10 during State 2. Rather, the requested vacuum level is monitored to determine when to exit State 2 of the vacuum control mode and return to State 1.

During State 2, the system controller 42 operates the peristaltic pump 22 using an open feedback loop to maintain the actual outflow rate of the peristaltic pump 22 at the maximum outflow rate ($F_{max}$) (at block 116). During State 2, the system controller 42 also maintains the diaphragm 14 in the normal position using a closed feedback loop (at block 117). In particular, the system controller 42 uses the signal from the sensor 36 representing the current position of the diaphragm 14 as feedback to monitor the current position of the diaphragm 14. The system controller 42 also transforms the current position of the diaphragm 14 into a vacuum setpoint ($V_{setpoint}$) (at block 118). As illustrated in FIG. 4, the system controller 42 continues to reset the vacuum setpoint based on the current position of the diaphragm 14 until State 2 ends. Accordingly, during State 2, the vacuum setpoint is used as the target vacuum level rather than the requested vacuum level initiated through the foot pedal. Therefore, as noted above, during State 2, the foot pedal does not control the vacuum level.

The system controller 42 provides the vacuum setpoint to the vacuum controller 34, and the vacuum controller 34 operates the vacuum pump 30 using a closed feedback loop to maintain the vacuum level in the second portion 18 of the chamber at the vacuum setpoint (at block 120, FIG. 4). An actual vacuum level ($V_{actual}$) is output by the vacuum sensor 32, which is provided to the vacuum controller 34 as feedback (and can also be displayed on the user interface 44 as noted above). As noted above, the foot pedal does not control the vacuum level during State 2 of the vacuum control mode. However, the requested vacuum level indicated by the foot pedal is monitored (at block 114) and, when the requested vacuum level is less than or equal to the vacuum setpoint (at block 122), the system controller 42 exits State 2 and returns to State 1 of the vacuum control mode (at block 107, FIG. 3).

Figure 11:
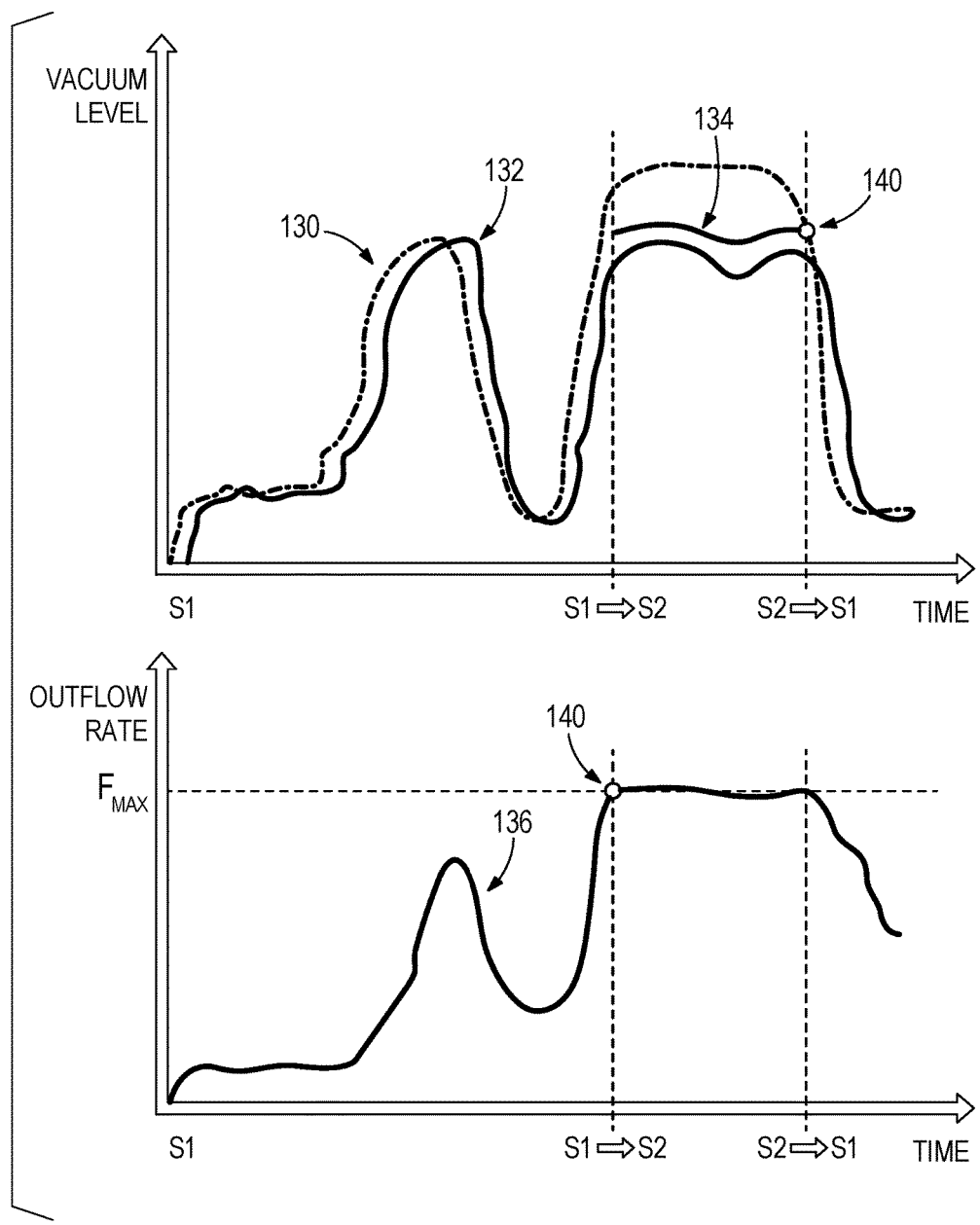
FIG. 11 is graph illustrating transitions between states of a vacuum control mode performed by the aspiration system of FIG. 1.

FIG. 11 illustrates transitions from State 1 to State 2 (labeled as "S1→S2") and from State 2 to State 1 (labeled as "S2→S1") within the vacuum control mode when the operator conducts a vacuum-cleaning procedure. Curve 130 represents the requested vacuum level (defined by foot pedal engagement). Curve 132 represents the actual vacuum level in the second portion 18 of the chamber 12. Curve 134 represents the vacuum setpoint set by the system controller 42 during State 2. Curve 136 represents the actual outflow rate of the peristaltic pump 22. Dots 140 mark the trigger events for the transitions between the states.

Flow Control Mode

Returning to FIG. 3, to operate the fluid management system 10 in the flow control mode, an operator selects the flow control mode from the list of operating modes presented on the user interface 44 (at block 150). The user interface 44 then prompts the operator to define operating parameters for the flow control mode (at block 152, FIG. 5). For the flow control mode, the operator specifies or selects a maximum outflow rate ($F_{max}$) and a maximum vacuum level ($V_{max}$), as described above with respect to the vacuum control model. The maximum outflow rate represents the maximum outflow rate when the foot pedal is in a lowest (i.e., fully engaged) position. The maximum outflow rate can be specified in cubic centimeters per minute ("cc/min").

In some embodiments, the user interface 44 displays a list of available values for each operating parameter or a list of available sets of values for the set of operating parameters. Furthermore, in some embodiments, the list of available values is customized based on the operator (e.g., linked to an operator identifier provided by the operator to the user interface 44, such as when the operator logs into the system 10).

Similar to the vacuum control mode, in some embodiments, the flow control mode has two states: State 1 and State 2. State 1 is the initial state. In State 1, the operator can increase (or decrease) the outflow rate of the peristaltic pump 22 by increasing (or decreasing) pressure on the foot pedal. In particular, the operator operates the foot pedal to indicate a requested outflow rate ($F_{request}$). The manually-requested outflow rate is based on the maximum outflow rate and the current position of the foot pedal.

The system controller 42 receives the manually-requested outflow rate (at block 154) and operates the peristaltic pump 22 using an open feedback loop to maintain the outflow rate at the requested outflow rate (at block 156). The system controller 42 also operates the vacuum pump 30 using a closed feedback loop to maintain the diaphragm 14 in the normal position (at block 158). In particular, the system controller 42 uses the signal from the sensor 36 representing the current position of the diaphragm 14 as feedback and provides operating parameters to the vacuum controller 34 based on the current position of the diaphragm. The vacuum controller 34 operates the vacuum pump 30 based on the received operating parameters. During State 1, the vacuum sensor 32 detects the actual vacuum level in the second portion 18 of the chamber 12 (at block 160). As noted above, this value can be displayed to the operator. In addition, if the actual vacuum level rises to or exceeds the maximum vacuum level (at block 162), the system controller 42 exits State 1 of the flow control mode and enters State 2.

Figure 6:
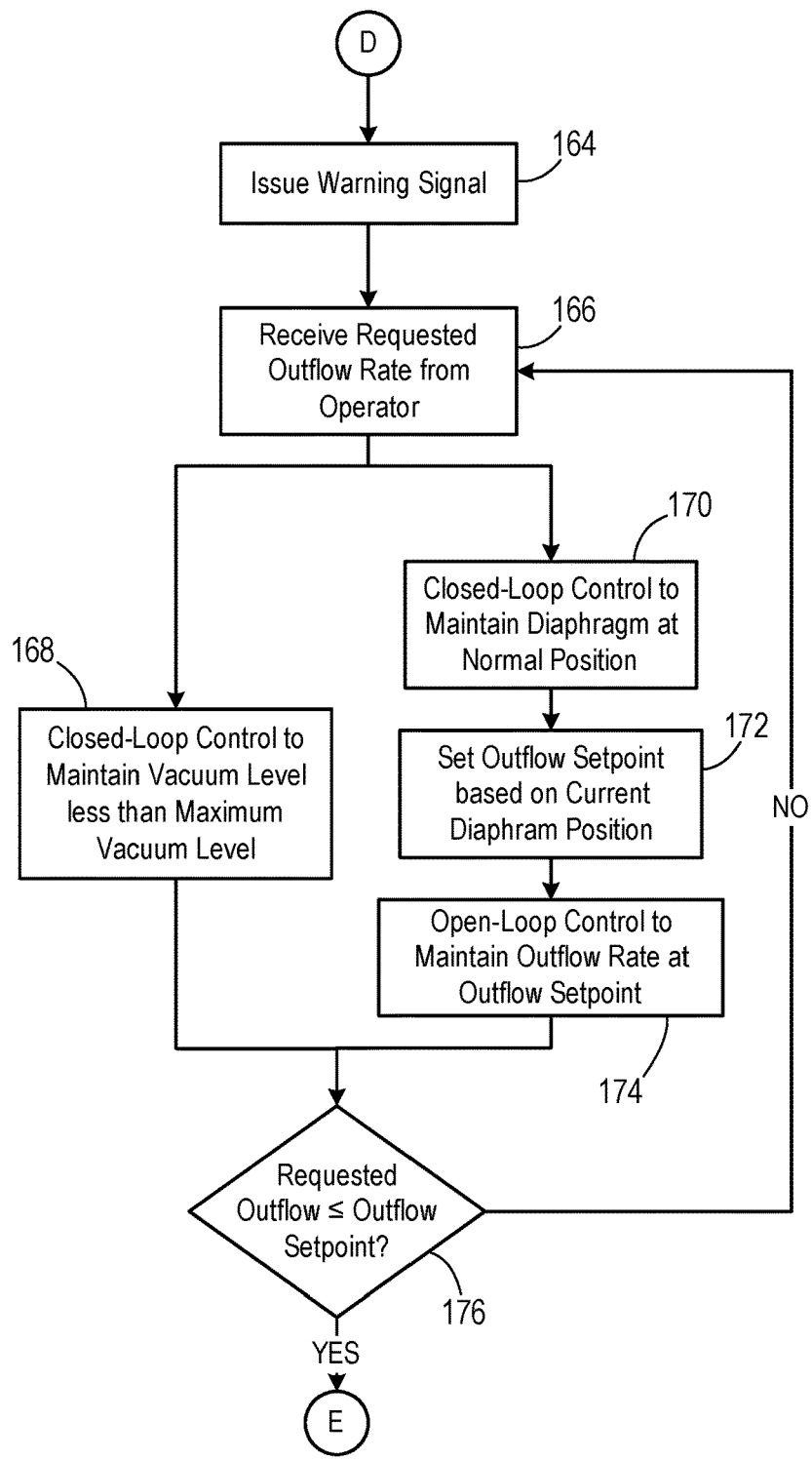
Figure 7:
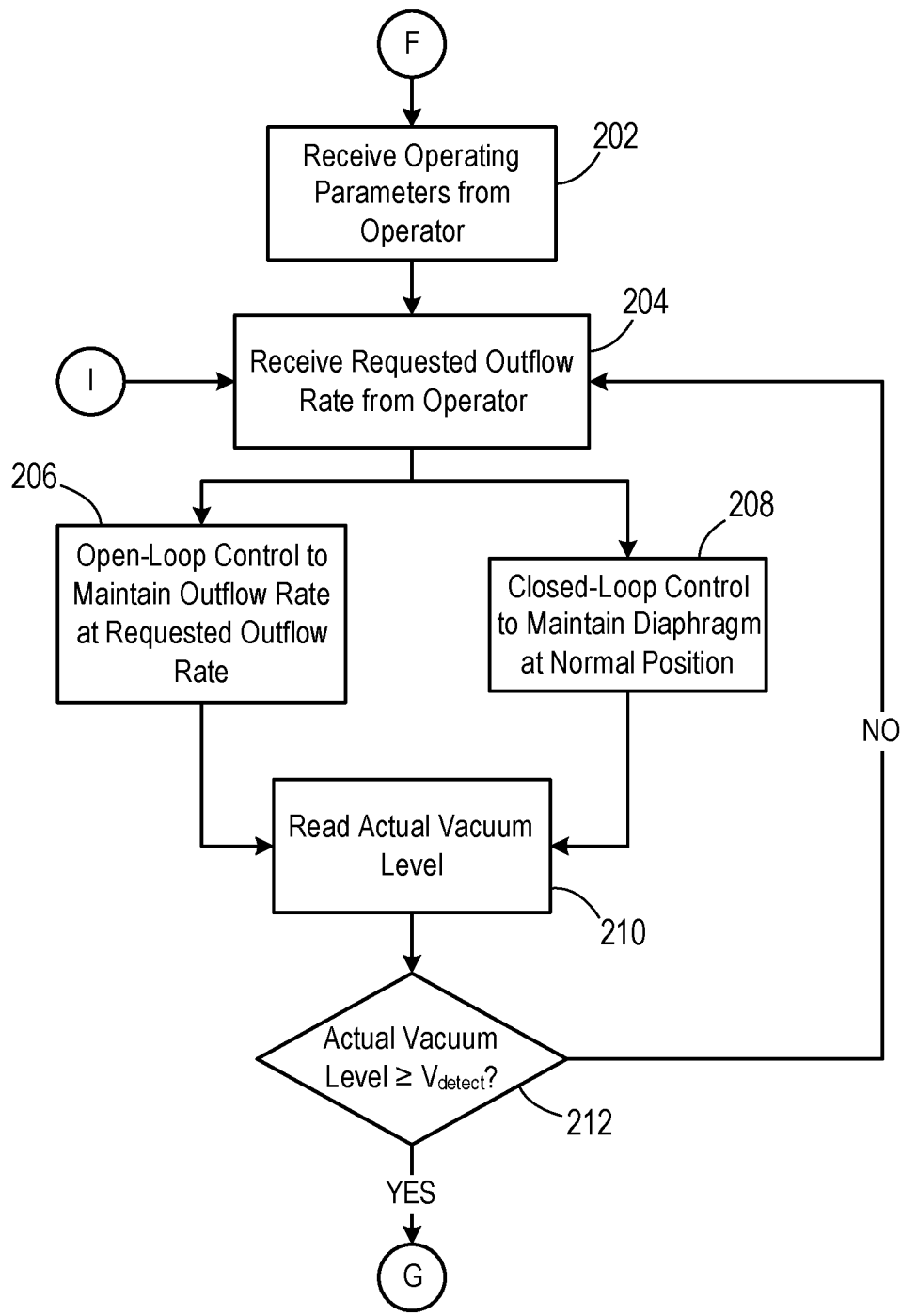

In some embodiments, the vacuum level rises to the maximum vacuum level within the flow control mode when an occlusion occurs. As illustrated in FIG. 6, when the system controller 42 detects an occlusion, the system 42 generates a warning signal (at block 164). The warning signal can include an audible and/or visual warning that informs the operator that an occlusion has been detected and that the operator should operate the fluid management system 10 accordingly.

In State 2 of the flow control mode, the operator operates the foot pedal to set a manually-requested outflow rate (at block 166, FIG. 6). However, as described in more detail below, the foot pedal does not control the outflow rate during State 2. Rather, the requested outflow rate is monitored to determine when to exit State 2 of the flow control mode and return to State 1.

During State 2, the vacuum controller 34 operates the vacuum pump 30 using a closed feedback loop to maintain the vacuum level in the second portion 18 of the chamber at the maximum vacuum level ($V_{max}$) (at block 168). In particular, the system controller 42 provides the maximum vacuum level to the vacuum controller 34, and the vacuum controller 34 uses the signal from the vacuum sensor 32 representing the current vacuum level as feedback. As noted above, the actual vacuum level can also be displayed to the operator.

Figure 3:
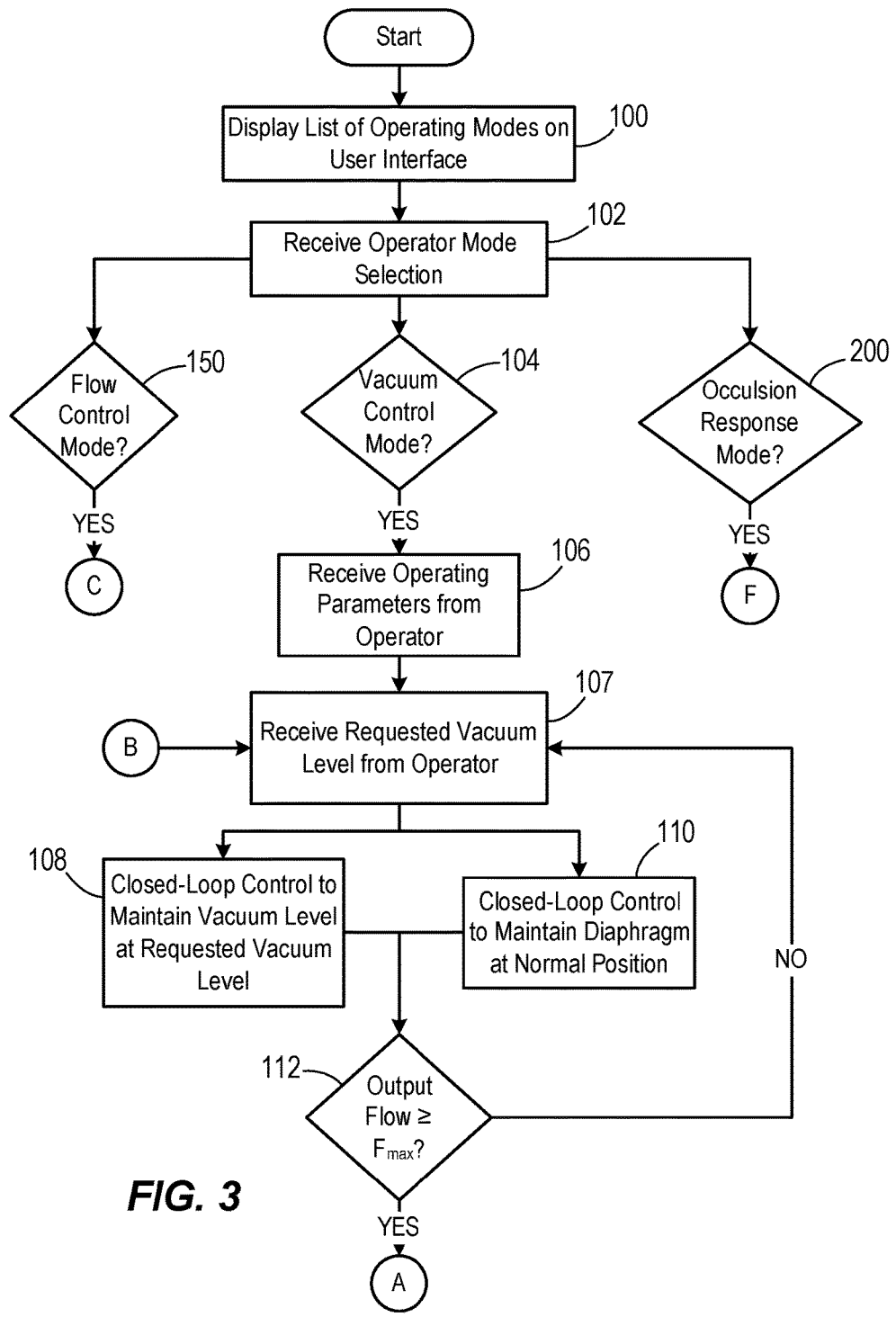
FIGS. 3-10 are flowcharts illustrating operation of the aspiration system of FIG. 1 in various operating modes.

During State 2, the system controller 42 also maintains the diaphragm 14 in the normal position using a closed feedback loop (at block 170). In particular, the signal from the sensor 36 representing the current position of the diaphragm 14 is used by the controller 42 as feedback. The system controller 42 also transforms the current position of the diaphragm 14 into an outflow setpoint ($F_{setpoint}$) (at block 172). As illustrated in FIG. 3, the system controller 42 continues to set the outflow setpoint based on the current position of the diaphragm 14 until State 2 ends. Accordingly, during State 2, the system controller 42 uses the outflow setpoint as the target outflow rate rather than the requested outflow rate initiated through the foot pedal. Therefore, as noted above, during State 2, the foot pedal does not control the outflow rate.

During State 2, the system controller 42 also operates the peristaltic pump 22 using an open feedback loop to maintain the outflow rate at the outflow setpoint (at block 174). As noted above, the foot pedal does not control the outflow rate during State 2 of the flow control mode. However, the requested outflow rate indicated by the foot pedal is monitored (at block 166) and, when the requested outflow rate is less than or equal to the outflow setpoint (at block 176), the system controller 42 exits State 2 and returns to State 1 of the flow control mode (at block 154, FIG. 5).

Figure 12:
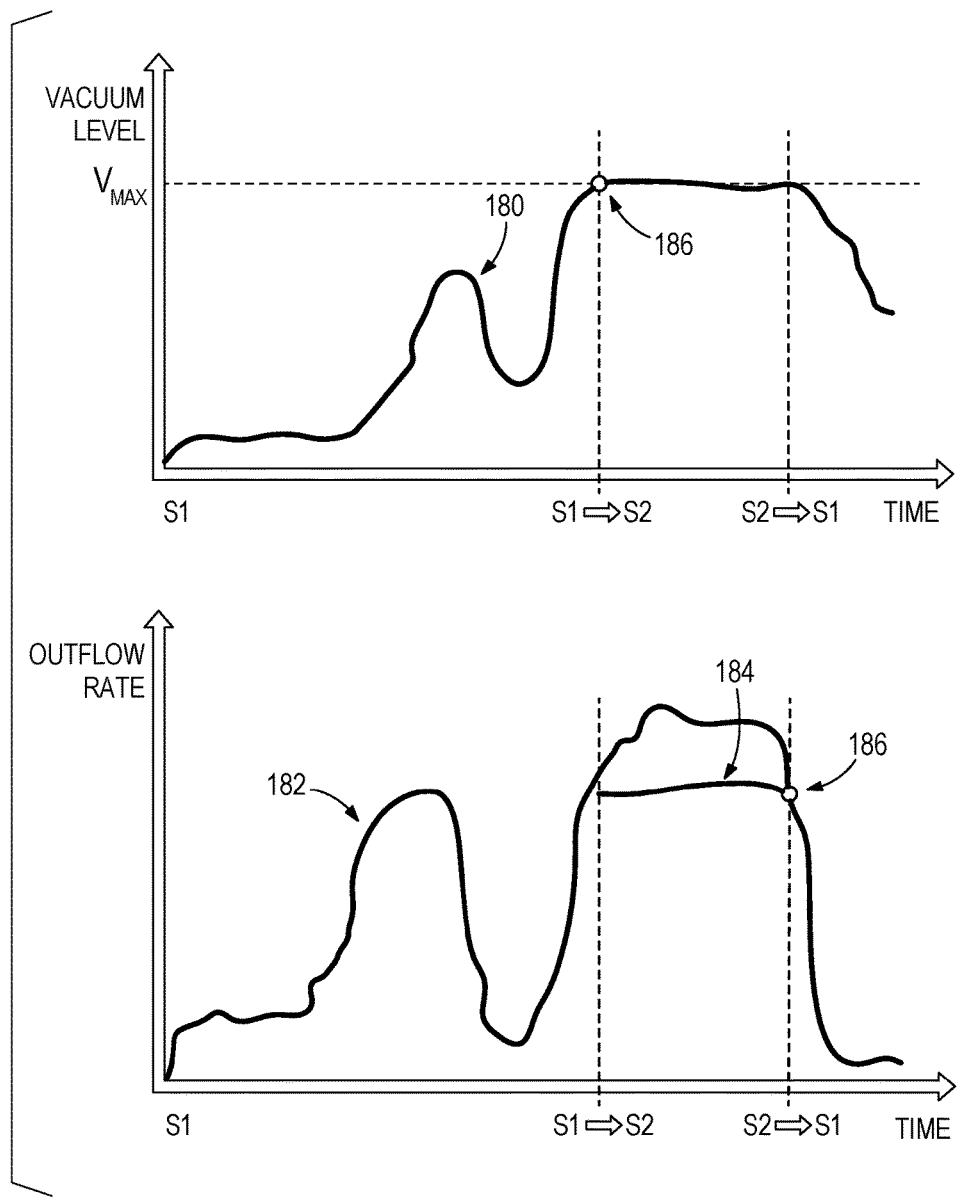
FIG. 12 is graph illustrating transitions between states of a flow control mode performed by the aspiration system of FIG. 1.

FIG. 12 illustrates transitions from State 1 to State 2 (labeled as "S1→S2") and from State 2 to State 1 (labeled as "S2→S1") within the flow control mode. Curve 180 represents the requested outflow rate defined by foot pedal engagement. Curve 182 represents the outflow setpoint set by the system controller 42 in the State 2. Curve 184 represents the actual vacuum level in the second portion 18 of the chamber 12. Dots 186 mark the trigger events causing the transition between the states.

Occlusion Response Mode

Returning to FIG. 3, to operate the fluid management system 10 in the occlusion mode, an operator selects the occlusion response mode from the list of operating modes presented on the user interface 44 (at block 200). The user interface 44 then prompts the operator to define operating parameters for the occlusion response mode (at block 202, FIG. 7). For the occlusion response mode, the operator specifies or selects a maximum outflow rate ($F_{max}$), an occlusion detection vacuum level ($V_{detect}$), and an occlusion hold vacuum level ($V_{hold}$). As described above for the flow control mode, the maximum outflow rate represents the maximum outflow rate when the foot pedal is in a lowest (i.e., fully engaged) position. The occlusion detection vacuum level represents a vacuum level used to detect an occlusion, and the occlusion hold vacuum level represents a vacuum level used after an occlusion is detected The occlusion response mode has four states: State 1, State 2, State 3, and State 4. State 1 is the initial state. In some embodiments, State 1 is the same as State 1 in the flow control mode (with an exception of the exit condition). In particular, in State 1, the operator can increase (or decrease) the outflow rate from the peristaltic pump 22 by increasing (or decreasing) pressure on the foot pedal. In particular, the operator operates the foot pedal to indicate a requested outflow rate ($F_{request}$). The manually-requested outflow rate is based on the maximum outflow rate and the current position of the foot pedal.

During State 1, the system controller 42 receives the manually-requested outflow rate (at block 204) and operates the peristaltic pump 22 using an open feedback loop to maintain the outflow rate at the requested outflow rate (at block 206). The system controller 42 also operates the vacuum pump 30 using a closed feedback loop to maintain the diaphragm 14 in the normal position (at block 208). In particular, the system controller 42 uses the signal from the sensor 36 representing the current position of the diaphragm 14 as feedback and provides operating parameters to the vacuum controller 34 based on the current position. The vacuum controller 34 operates the vacuum pump 30 based on the received operating parameters.

During State 1, the vacuum sensor 32 also detects the actual vacuum level in the second portion 18 of the chamber 12 (at block 210). As noted above, this value can be displayed to the operator. In addition, if the actual vacuum level rises to or exceeds the occlusion detection vacuum level ($V_{detect}$) (at block 212), the system controller 42 exits State 1 of the occlusion response mode and enters State 2.

Figure 8:
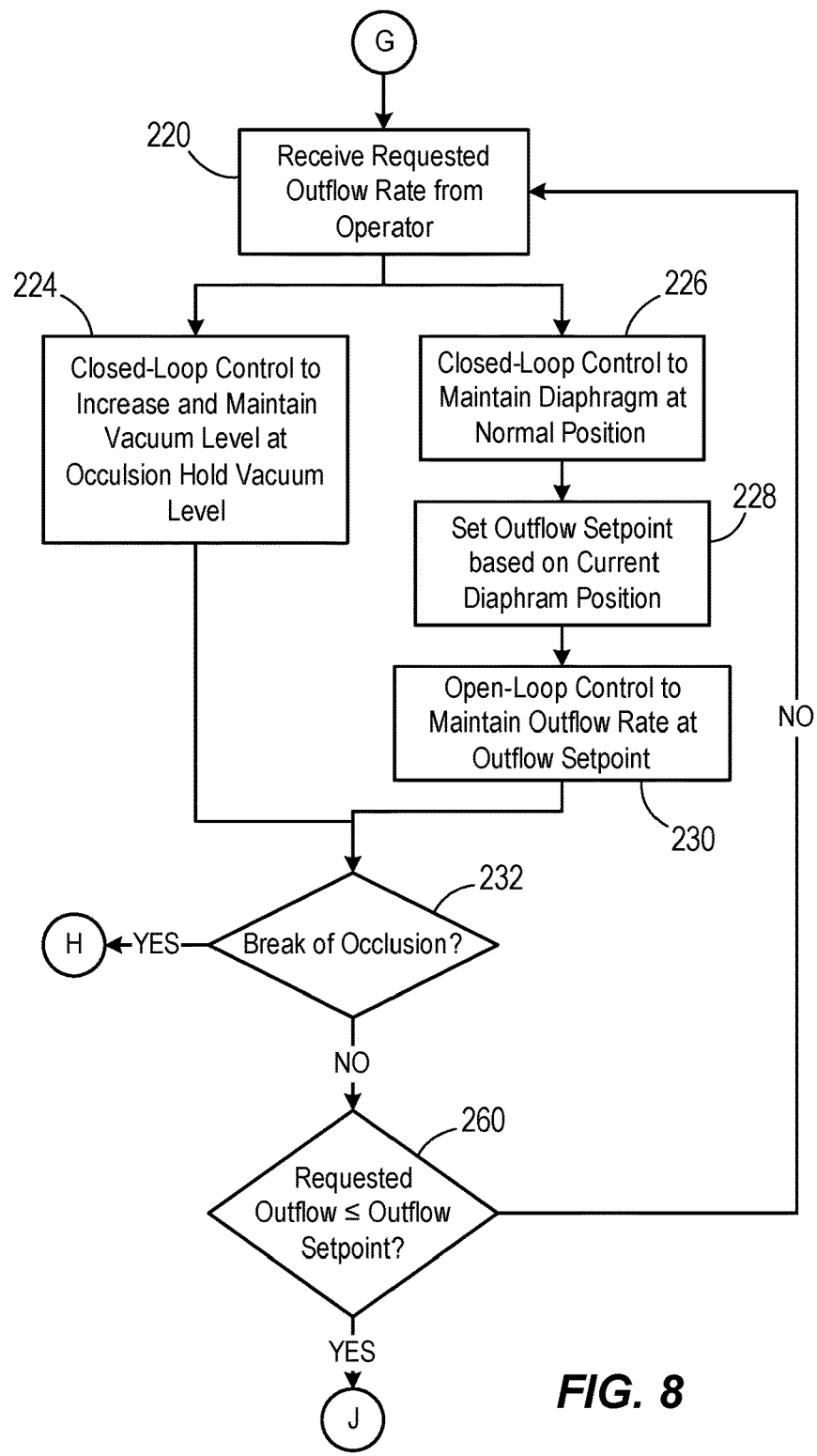

In State 2 of the occlusion response mode, the operator operates the foot pedal to set a manually-requested outflow rate (at block 220, FIG. 8). However, as described in more detail below, the foot pedal does not control the outflow rate during State 2. Rather, the requested outflow rate is monitored to determine when to exit State 2 of the occlusion response mode and return to State 1.

During State 2, the vacuum controller 34 operates the vacuum pump 30 using a closed feedback loop to increase and maintain the vacuum level in the second portion 18 of the chamber 12 at the occlusion hold vacuum level ($V_{hold}$) (at block 224). In particular, the system controller 42 provides the occlusion hold vacuum level to the vacuum controller 34, and the vacuum controller 34 uses the signal from the vacuum sensor 32 representing the current vacuum level as feedback to raise the vacuum level to the occlusion hold vacuum level. As noted above, the actual vacuum level detected by the vacuum sensor 32 can also be displayed to the operator. Maintaining the vacuum level at the occlusion hold vacuum level grasps the captured material (i.e., the obstruction) and, in some situations, frees or breaks the obstruction.

During State 2, the system controller 42 also maintains the diaphragm 14 in the normal position using a closed feedback loop (at block 226). In particular, system controller 42 uses the signal from the sensor 36 representing the current position of the diaphragm 14 as feedback. The system controller 42 also transforms the current position of the diaphragm 14 into an outflow setpoint ($F_{setpoint}$) (at block 228). As illustrated in FIG. 8, the system controller 42 continues to set the outflow setpoint based on the current position of the diaphragm 14 until State 2 ends. Accordingly, during State 2, the system controller 42 uses the outflow setpoint as the target outflow rate rather than the requested outflow rate initiated through the foot pedal. Therefore, as noted above, during State 2, the foot pedal does not control the outflow rate.

During State 2, the system controller 42 also operates the peristaltic pump 22 using an open feedback loop to maintain the outflow rate at the outflow setpoint (at block 230). During State 2, if the system controller 42 detects a "break of occlusion" condition (at block 232), the system controller 42 exits State 2 of the occlusion response mode and performs State 3. In some embodiments, the system controller 42 detects a "break of occlusion" condition based on signals from the diaphragm position sensor 36. In particular, the system controller 42 can be configured to detect a "break of occlusion" condition when rapid movement of the diaphragm 14 toward the diaphragm's limited position is detected by the diaphragm position sensor 36. In particular, when an obstruction is broken or removed, the diagram 14 will experience a rapid fluctuation in position as pressure is released from the chamber 12.

Figure 9:
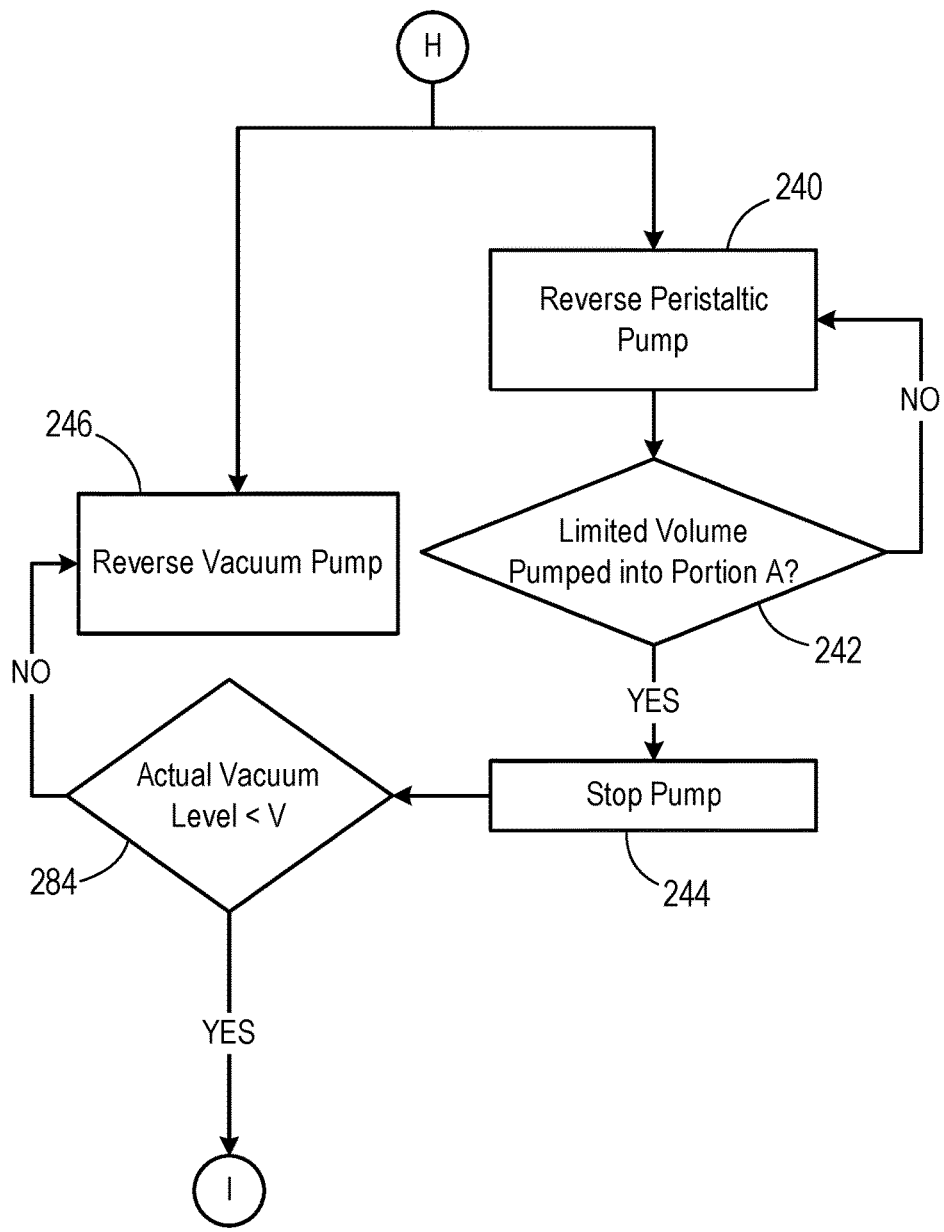

In State 3, a break of the occlusion has been detected. Therefore, the high vacuum level that was used to grasp the obstruction is no longer necessary and, if maintained, could adversely affect the procedure. Accordingly, in State 3, the system controller 42 automatically controls the fluid management system 10 to return the fluid management system 10 to a state before the occlusion was detected (i.e., State 1). In particular, as illustrated in FIG. 9, the system controller 42 reverses operation of the peristaltic pump 22 (at block 240) until a volume equivalent to the limited volume is pumped back into the first portion 16 of the chamber 12 (at block 242). The system controller 42 then stops the pump 22 (at block 244). In addition, the vacuum controller 34 reverses the vacuum pump 30 to drop the vacuum level in the second portion 18 of the chamber 12 below the occlusion detection vacuum level (e.g., based on operating parameters provided by the system controller 42) (at block 246). When the actual vacuum level drops below the occlusion detection vacuum level (at block 248), the system controller 42 exits State 3 and returns to State 1 of the occlusion response mode.

Figure 13:
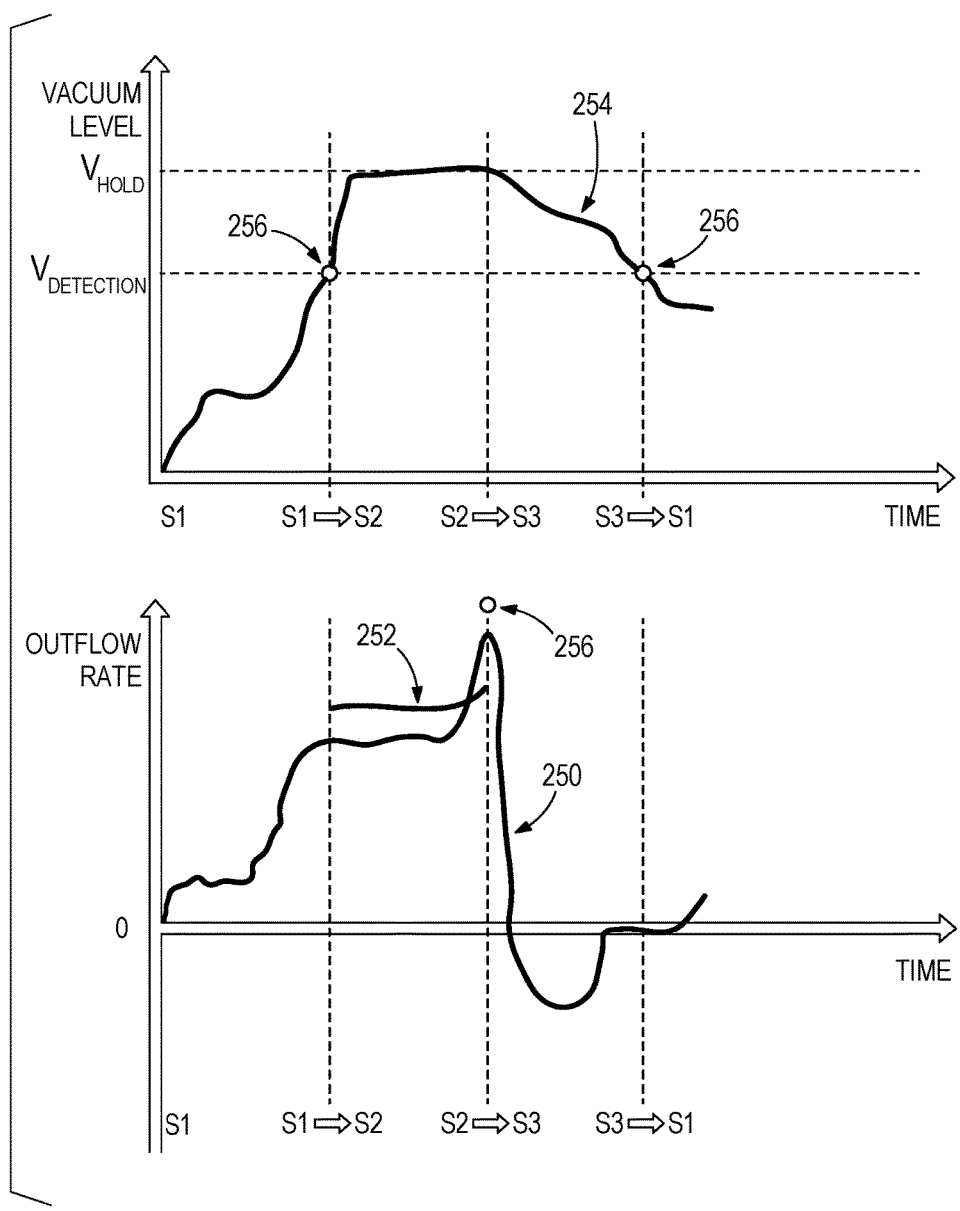
FIGS. 13-14 are graphs illustrating transitions between states of an occlusion response mode performed by the aspiration system of FIG. 1.

FIG. 13 shows transitions between State 1 and State 2 (labeled as "S1→S2"), State 2 and State 3 (labeled as "S2→S3"), and State 3 and State 1 (labeled as "S3→S1") of the occlusion response mode. Curve 250 represents the actual outflow rate. Curve 252 represents the outflow setpoint set by the system controller 42 in State 2. Curve 254 represents the actual vacuum level in the second portion 18 of the chamber 12. Dots 256 mark trigger events that cause the transitions between the states.

Figure 10:
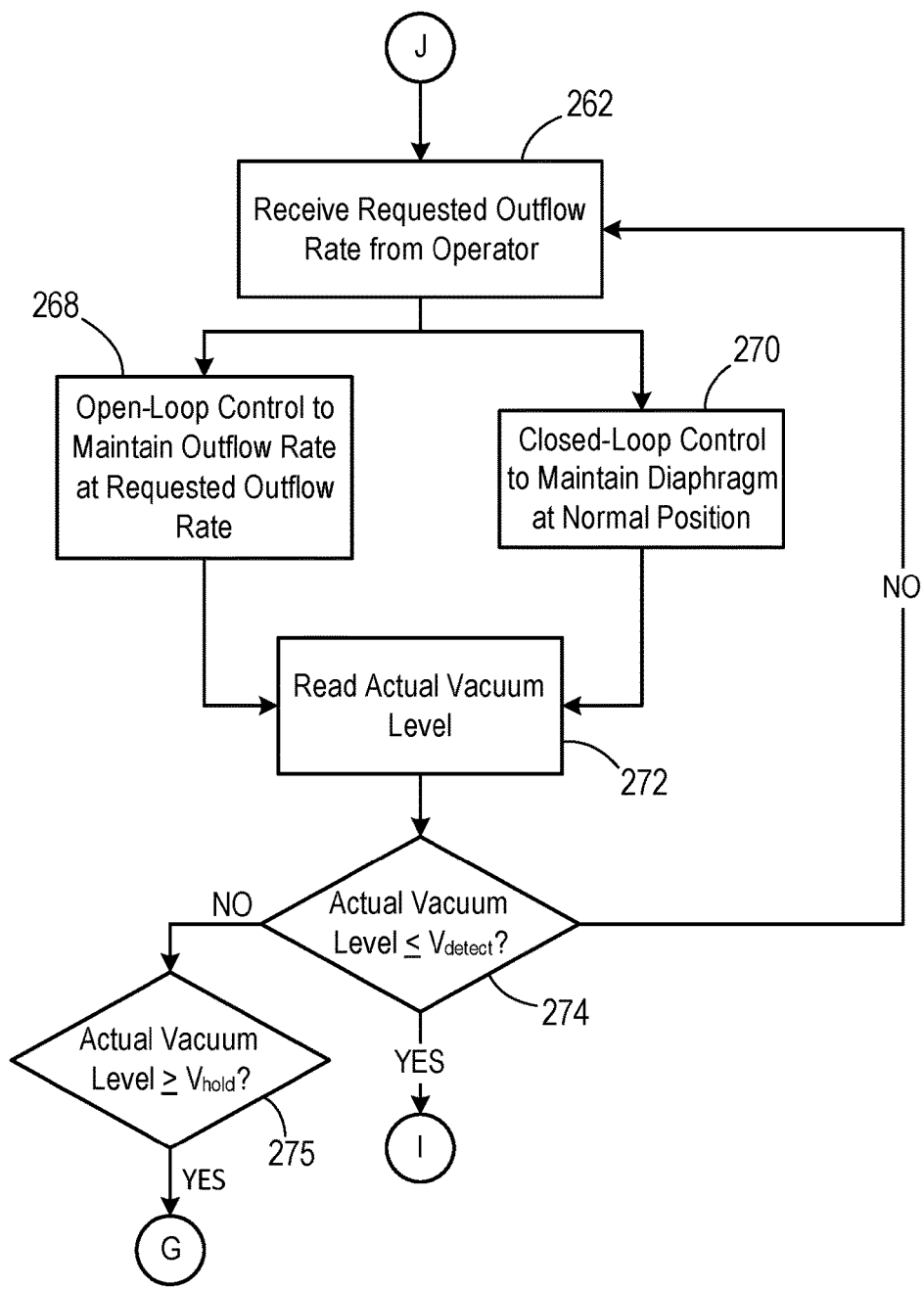

Returning to FIG. 8, if a break of occlusion is not detected in State 2 (at block 232, FIG. 8) but the requested outflow value (i.e., based on foot pedal pressure) is equal to or less than the outflow setpoint (at block 260), the system controller 42 exits State 2 and performs State 4 of the occlusion response mode. In State 4, the fluid management system 10 can be returned to normal operation (i.e., where no obstruction is detected) even if the "break of occlusion" condition was not detected. In particular, if there is only a partial obstruction and the available outflow rate is sufficient to satisfy the operator's outflow request (through the foot pedal), the occlusion response mode transitions to State 4 where normal operation resumes. For example, as illustrated in FIG. 10, in State 4, the operator can increase (or decrease) the outflow rate from the peristaltic pump 22 by increasing (or decreasing) pressure on the foot pedal. In particular, the operator operates the foot pedal to indicate a requested outflow rate ($F_{request}$). The manually-requested outflow rate is based on the maximum outflow rate and the current position of the foot pedal.

During State 4, the system controller 42 receives the manually-requested outflow rate (at block 262) and operates the peristaltic pump 22 using an open feedback loop to maintain the outflow rate at the requested outflow rate (at block 268). The system controller 42 also operates the vacuum pump 30 in a closed feedback loop to maintain the diaphragm 14 in the normal position (at block 270). In particular, the system controller 42 uses the signal from the sensor 36 representing the current position of the diaphragm 14 as feedback and provides operating parameters to the vacuum controller 34 based on the current position. The vacuum controller 34 operates the vacuum pump 30 based on the received operating parameters. During State 4, the vacuum sensor 32 also detects the actual vacuum level in the second portion 18 of the chamber 12 (at block 272). This value can be displayed to the operator. In addition, if the actual vacuum level falls below the occlusion detection vacuum level (at block 274), the system controller 42 exits State 4 of the occlusion response mode and returns to State 1. If the actual vacuum level rises to the occlusion hold vacuum level (at block 275), system controller 42 exits State 4 of the occlusion response mode and returns to State 2.

Figure 14:
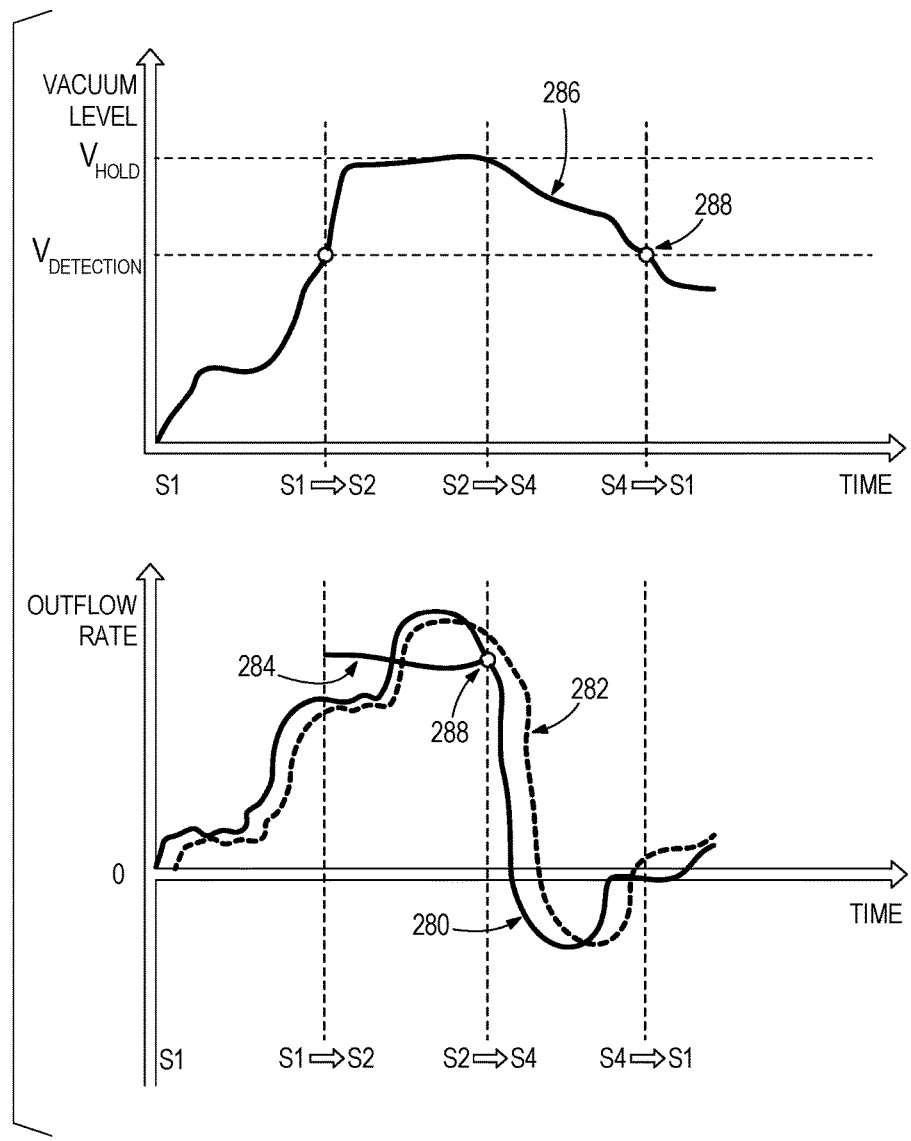

FIG. 14 shows transitions between State 1 and State 2 (labeled as "S1→S2"), State 2 and State 4 (labeled as "S2→S4"), and State 4 and State 1 (labeled as "S3→S1") of the occlusion response mode. Curve 280 represents the requested outflow rate. Curve 282 represents the actual outflow rate. Curve 284 represents the outflow setpoint set by the system controller 42 in State 2. Curve 286 represents the actual vacuum level in the second portion 18 of the chamber 12. Dots 288 mark the occurrence of trigger events that cause the state transitions.

It should be understood that in some embodiments, the system controller 42 is configured to automatically switch the operating mode of the fluid management system 10 based on feedback received by the system controller 42. For example, in some embodiments, when the system controller 42 detects an occlusion, the system controller 42 can be configured to automatically switch the fluid management system 10 to the occlusion response mode (or a particular state of the occlusion response mode). Furthermore, it should be understood that the fluid management system 10 can include additional modes than those described above and each operating modes described herein can include additional states than those described above.

Figure 15:
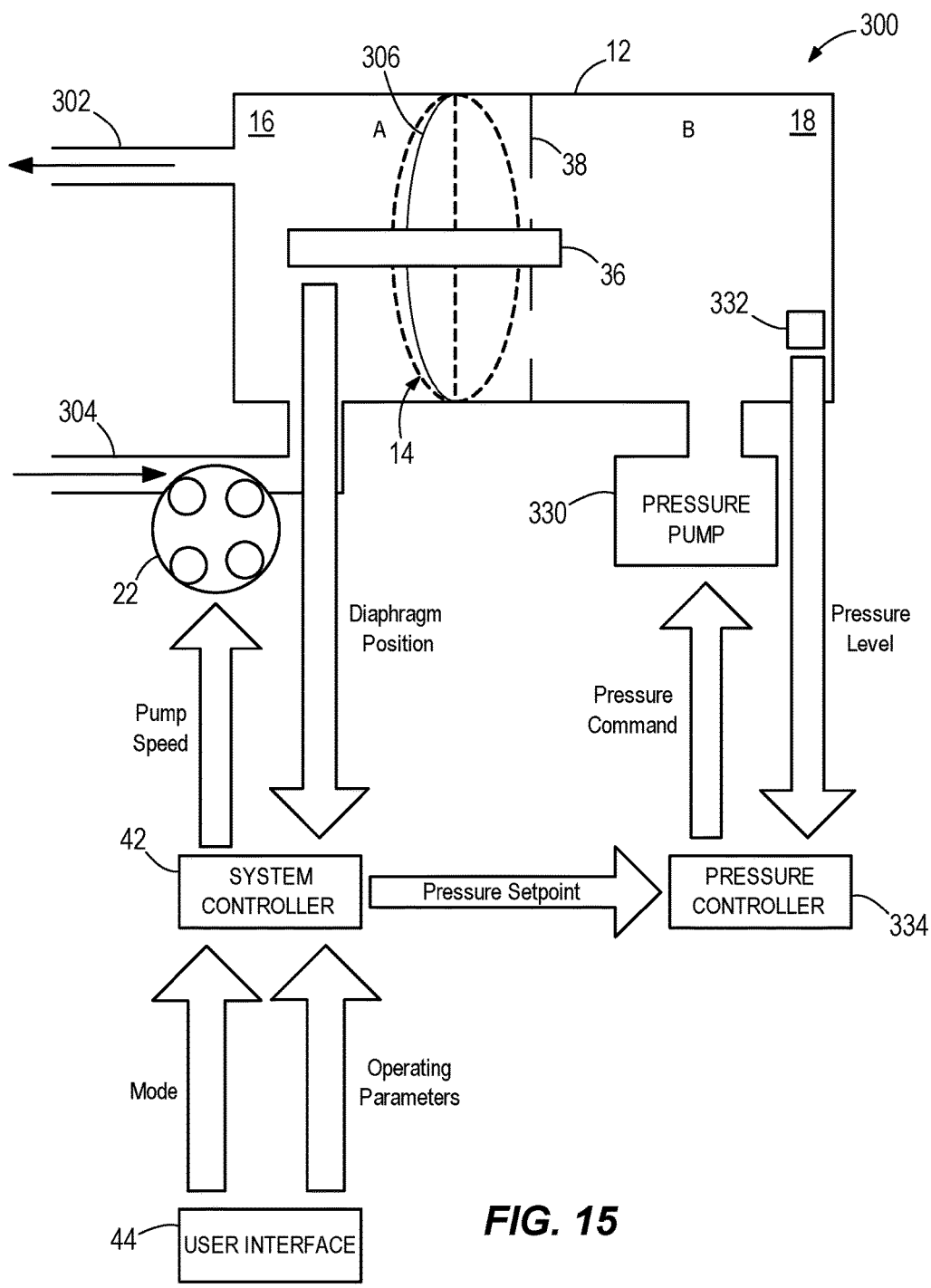
FIG. 15 schematically illustrates an infusion system.

Components of the fluid management system 10 can also be used to control the infusion of fluids into the patient's eye. For example, FIG. 15 illustrates an infusion system 300. Similar to the system 10, the system 300 includes the chamber 12 with the flexible diaphragm 14 (and optionally the barrier 38) and the sensor 36 for detecting a position of the diaphragm 14. The system 300 also includes the peristaltic pump 22 and the system controller 42 connected to the user interface 44. Analogous to the vacuum components in the aspiration system, the infusion system includes a pressure pump 330, a pressure sensor 332 and a pressure controller 334. Unlike the system 10, the first portion 16 of the chamber 12 included in the system 300 is connected with an output line 302 that provides a fluid to the patient's eye during a surgical procedure. The first portion 16 of the chamber is also connected to a supply line 304 that supplies the fluid to the first portion 16 from an external fluid source (e.g., a bottle or bag of fluid). Accordingly, the peristaltic pump 22 can be operated (e.g., using a control or foot pedal (not shown)) to control the amount and/or pressure of fluid drawn from the external fluid source (not shown) and supplied to the patient's eye.

The system 300 can be operated similar to the fluid management system 10 described above. For example, the system 300 can be operated in one or more different modes, and, in each mode, the system controller 42 can be configured to operate the pump 22 and/or the pressure pump 330 to keep the diaphragm 14 in a predetermined position. In particular, the system controller 42 can use feedback loops that use feedback from the diaphragm position sensor 36 to control the flow rate of the peristaltic pump 22 and the gas pressure in the second portion 18 to satisfy various surgical objectives (e.g., an increased infusion rate, a decreased infusion rate, a steady infusion rate, etc.). For example, the pressure pump 330 is used to control the gas pressure in the second portion 18 of the chamber. In the fluid management system 10, the pressure in the second portion 18 is maintained below ambient pressure to create a suction force that removes fluids from the patient's eye. Alternatively, in the infusion system 300, the pressure in the second portion 18 is maintained above ambient pressure to create an output force for the fluids supplied to the patient's eye.

In a first mode of operation (pressure or vacuum control), the system controller 42 responds to inputs through the operator interface 44 to set the pressure setpoint. Pressure controller 334 operates pressure pump 330 so as to maintain the output of pressure sensor 332 at the pressure setpoint level selected by the operator. Simultaneously, the system controller 42 adjusts the pump speed of peristaltic pump 22 to maintain the diaphragm 14 at a predetermined position, as determined by the signal from the diaphragm position sensor 36. The pump speed can be used to calculate the inflow rate through the supply line 304, which must be equal to the outflow rate through the output line 302. This assumed inflow rate may be displayed or otherwise used to affect the operation of the system.

In a second mode of operation (flow control), the system controller 42 responds to inputs through the operator interface 44 to set the pump speed corresponding to a flow rate selected by the operator. The peristaltic pump 22 operates at this pump speed, thereby maintaining the inflow rate through the supply line 304 at the selected flow rate. Simultaneously, the system controller 42 adjusts the pressure setpoint to pressure controller 334 to maintain the diaphragm 14 at a predetermined position, as indicated by the signal from the diaphragm position sensor 36. The outflow rate through the output line 302 should then be equal to the operator-selected inflow rate through the supply line 304. The pressure setpoint to pressure controller 334 and/or the resulting actual pressure signal from pressure sensor 332 may be displayed or otherwise used to affect the operation of the system.

In some embodiments, an aspiration system 10 and an infusion system 300 are linked through a common system controller 42 to form an integrated fluid management system. In such a system, the operation of the infusion system 300 may be adjusted in real time to respond to changing conditions in the aspiration system 10, so as to maintain a safe balance between fluids entering and leaving the eye. For example, the actual flow out of the eye derived from the operating parameters of aspiration system 10 might be used to set the flow into the eye (pump speed) for the infusion system 300 operating in the second mode of operation described above.

Figure 16:
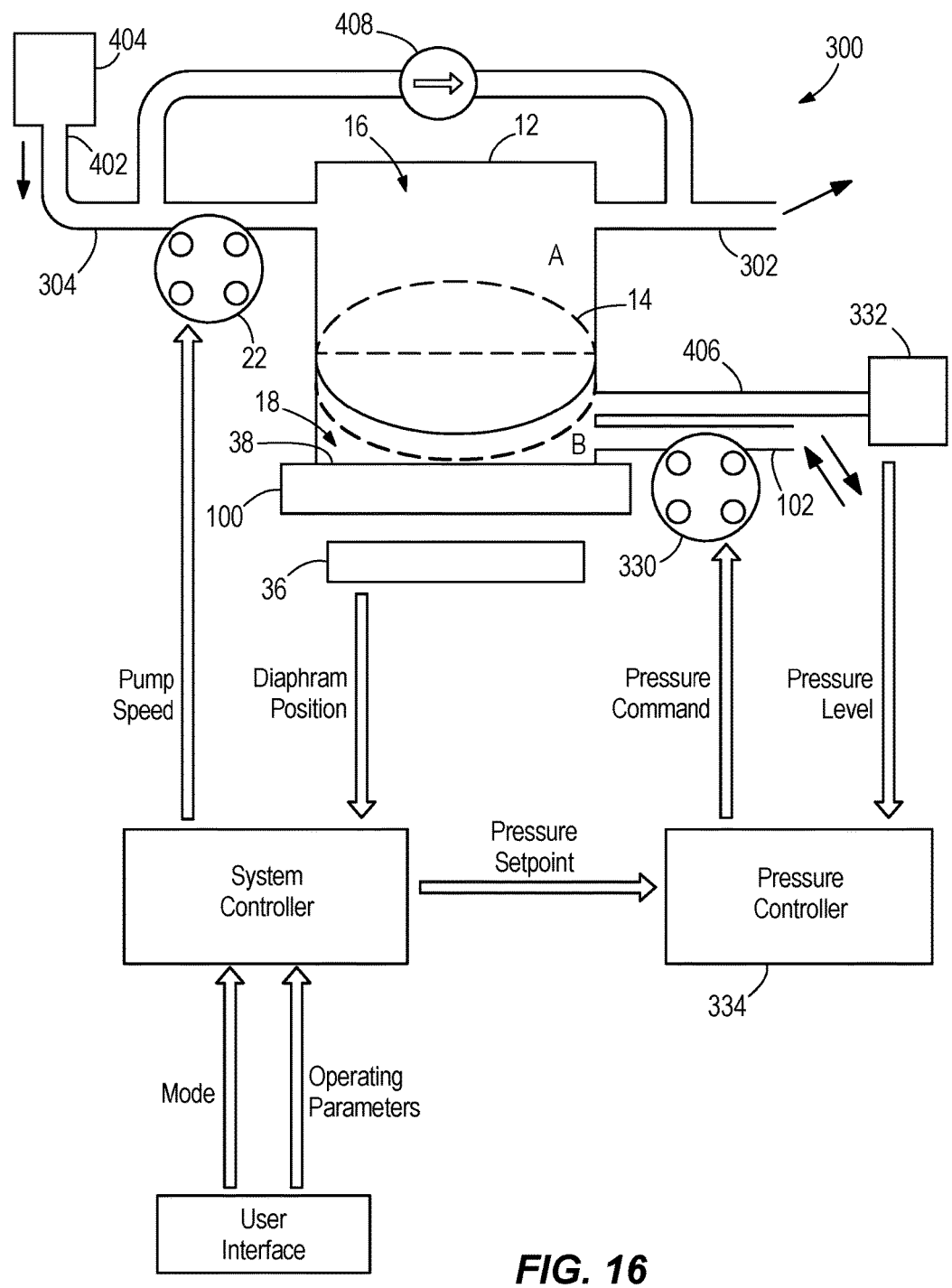
FIG. 16 schematically illustrates another embodiment of an infusion system.

FIG. 16 illustrates another embodiment of infusion system 300. The diaphragm position sensor 36 is a non-contacting, optical-type positioned to view the diaphragm 14 through a transparent window 100. The transparent window 100 also serves as part of the enclosure of chamber 12. In addition to peristaltic pump 22 (connected through supply line 304 and vented administration set 402 to fluid bottle 404) the pressure pump 330 is also a peristaltic type pump. The pressure pump 330 is connected to second portion 18 of the chamber 12 and also to the atmosphere through vent line 102. Pressure controller 334 operates peristaltic pump 330 bi-directionally. Pumping air from the vent line 102 to the chamber 12 increases the pressure level in the second portion 18 of the chamber 12, and pumping air from the chamber 12 to the vent line 102 decreases the pressure level. Pressure sensor 332 communicates with the second portion 18 of the chamber 12 through pressure port 406, providing a feedback signal to pressure controller 334. The first portion 16 of chamber 12 is also connected through output line 302 to various surgical instruments used in the patient's eye during a surgical operation.

Figure 17A:
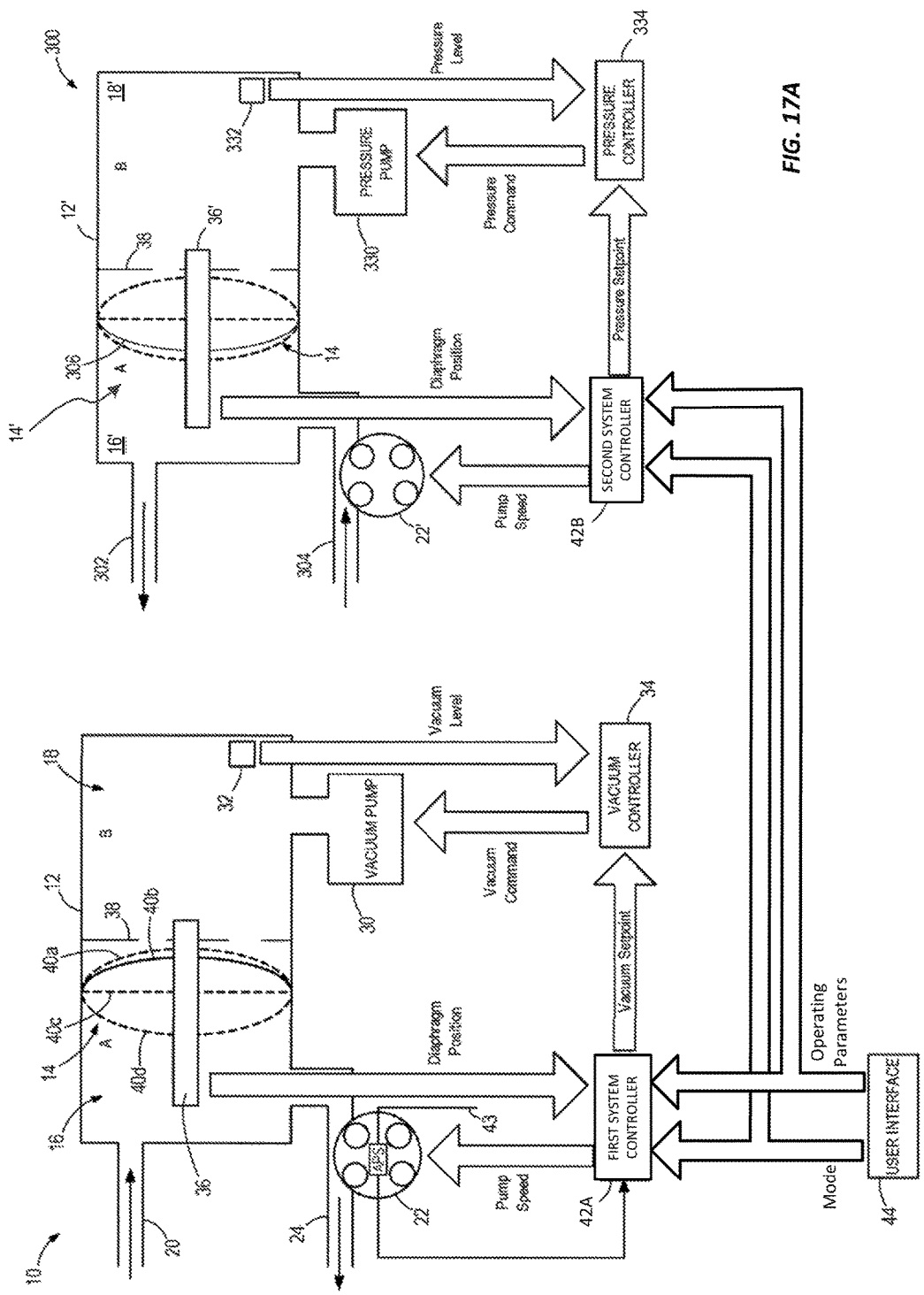
FIG. 17A schematically illustrates a system combining an aspiration system and an infusion system.

The embodiment shown in FIG. 16 also incorporates a fail-safe feature to ensure that at least some minimum level of infusion pressure is maintained at all times. The one-way valve 408 is connected to permit flow from supply line 304 to output line 302. Fluid bottle 404 is suspended above the level of the chamber 12 such that the pressure (due to gravity) delivered through the vented administration set 402 to the supply line 304 is at a level adequate to maintain the pressure in the eye at a minimum safe level. In the event that peristaltic pump 22 fails to operate, the pressure level in output line 302 will fall as the fluid in chamber 12 is used up. At the point where this pressure level falls to the same level as the pressure in supply line 304, one-way valve 408 will open and fluid flow to the eye will be maintained at that pressure level In yet another embodiment, various features and aspects of embodiments described above may be combined to form an integrated ocular fluid management system (FIG. 17A). The system can include a first chamber 12 having a first portion 16 and a second portion 18. The first portion is connected to a first input line 20 communicating with the first portion of the first chamber and a first output line 24 communicating with the first portion of the first chamber. The system may also include a second chamber 12' having a first portion 16' and a second portion 18'. The first portion is connected to a second input line 304 communicating with the first portion of the second chamber and a second output line 302 communicating with the first portion of the second chamber.

A first pump 22 communicates with the first output line and a second pump 22' communicates with the second input line. A first pressure regulator 30 communicates with the second portion of the first chamber and has a range of operation including pressures less than ambient. A second pressure regulator 330 communicates with the second portion of the second chamber and has a range of operation including pressures greater than ambient. A first diaphragm 14 is contained in the first chamber and configured to change position based on a pressure difference between the first portion and the second portion of the first chamber. A second diaphragm 14' is contained in the second chamber and is configured to change position based on a pressure difference between the first portion and the second portion of the second chamber. A first sensor 36 detects a position of the first diaphragm and transmits a first signal based on the detected position. A second sensor 36' detects a position of the second diaphragm and transmits a second signal based on the detected position. A first controller 42A is configured to receive the first signal and control operation of at least one of the first pump and the first pressure regulator based on the first signal to maintain the first diaphragm in a predetermined position. A second controller 42B is configured to receive the second signal and control operation of at least one of the second pump and the second pressure regulator based on the second signal to maintain the second diaphragm in a predetermined position.

Figure 17B:
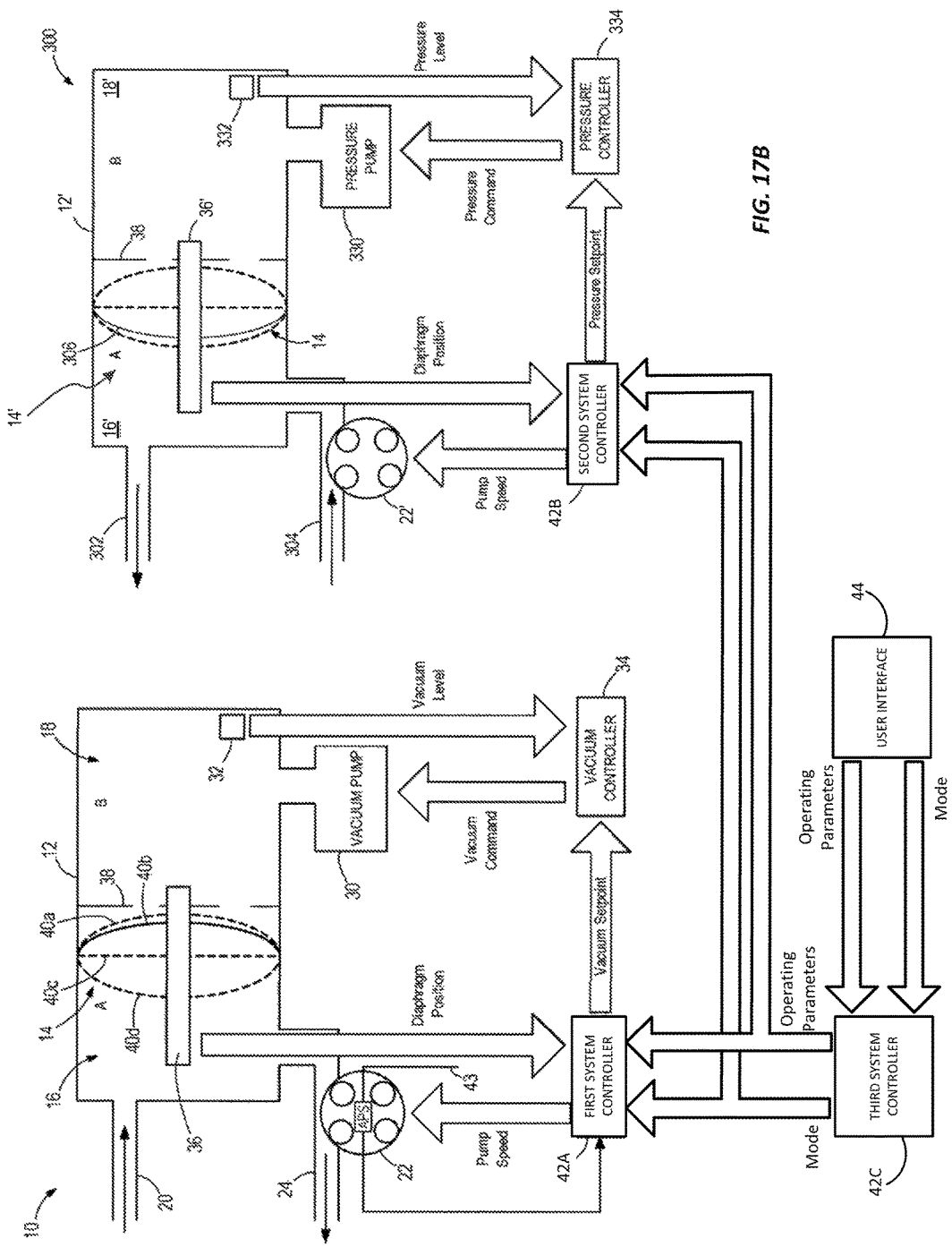
FIG. 17B schematically illustrate a system combining an aspiration system and an infusion system, with an additional controller.
Figure 17C:
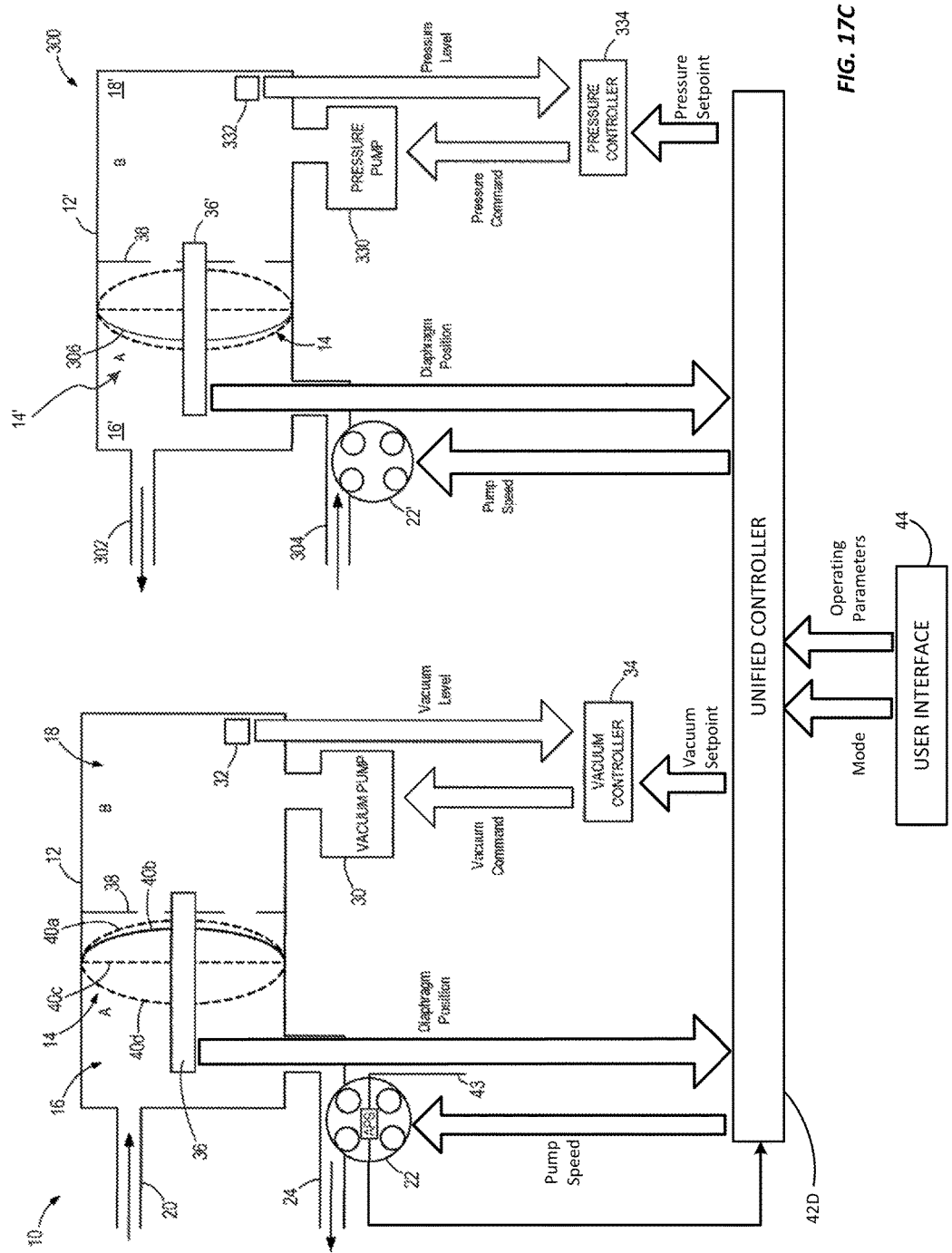
FIG. 17C schematically illustrates a system combining an aspiration system and an infusion system and a unified controller.

The integrated ocular fluid management system may also include a third controller 42C (FIG. 17B) to coordinate the operation of the first controller 42A and the second controller 42B. Alternatively, the integrated ocular fluid management system may include a unified controller 42D (FIG. 17C) that encompasses the functions of the first, second, and third controllers 42A, 42B, and 42C.

The first controller 42A may be configured to determine a break of occlusion condition. The first controller 42A may also be configured to communicate the break of occlusion condition to at least one of the second and third controllers 42B and 42C.

The second controller 42B may be configured to respond to a break of occlusion condition by commanding the second pressure regulator to set a predetermined pressure in the second portion of the second chamber based on a pressure level in the fluid management system. The second controller 42B may also be configured to respond to a break of occlusion condition by commanding the second pressure regulator to set a predetermined pressure in the second portion of the second chamber greater than a normal operating pressure. The third controller 42C may have multiple modes of operation including at least one mode of operation in which the second controller 42B is coordinated to operate the second pump to maintain the flow in the second input line at a level equal to or greater than the flow in the first output line that the first controller 42A maintains by operation of the first pump.

Various features and aspects of the invention are set forth in the following claims.

What is claimed is:

1. An integrated ocular fluid management system, comprising:
    a first chamber including a first portion and a second portion, the first portion of the first chamber connected to a first input line communicating with the first portion of the first chamber and a first output line communicating with the first portion of the first chamber;
    a second chamber including a first portion and a second portion, the first portion of the second chamber connected to a second input line communicating with the first portion of the second chamber and a second output line communicating with the first portion of the second chamber;
    a first pump communicating with the first output line;
    a second pump communicating with the second input line;
    a first pressure regulator communicating with the second portion of the first chamber and having a range of operation including pressures less than ambient;
    a second pressure regulator communicating with the second portion of the second chamber and having a range of operation including pressures greater than ambient;
    a first diaphragm contained in the first chamber and configured to change position based on a pressure difference between the first portion and the second portion of the first chamber;
    a second diaphragm contained in the second chamber and configured to change position based on a pressure difference between the first portion and the second portion of the second chamber;

a first sensor for detecting a position of the first diaphragm and transmitting a first signal based on the detected position of the second diaphragm;

a second sensor for detecting a position of the second diaphragm and transmitting a second signal based on the detected position of the second diaphragm;

a first controller configured to receive the first signal and control operation of at least one of the first pump and the first pressure regulator based on the first signal to maintain the first diaphragm in a predetermined position;

a second controller configured to receive the second signal and control operation of at least one of the second pump and the second pressure regulator based on the second signal to maintain the second diaphragm in a predetermined position; and a third controller to coordinate the operation of the first controller and the second controller.

2. The system of claim 1, wherein a unified controller encompasses the functions of the first controller, the second controller, and the third controller.

3. The system of claim 1, wherein the first controller is configured to determine a break of occlusion condition.

4. The system of claim 1, wherein the first controller is configured to communicate a break of occlusion condition to at least one of the second and third controllers.

5. The system of claim 4, wherein the second controller is configured to respond to the break of occlusion condition by commanding the second pressure regulator to set a predetermined pressure in the second portion of the second chamber based on a pressure level in the integrated ocular fluid management system.

6. The system of claim 4, wherein the second controller is configured to respond to the break of occlusion condition by commanding the second pressure regulator to set a predetermined pressure in the second portion of the second chamber greater than a normal operating pressure.

7. The system of claim 1, wherein the third controller has at least one mode of operation in which the second controller is coordinated to operate the second pump to maintain a flow in the second input line at a level equal to or greater than a flow in the first output line that the first controller maintains by operation of the first pump.

* * * * *